United States Patent
Glenn, Jr. et al.

(10) Patent No.: US 9,993,419 B2
(45) Date of Patent: Jun. 12, 2018

(54) METHOD OF TREATING HAIR WITH A CONCENTRATED CONDITIONER

(71) Applicant: The Procter & Gamble Company, Cincinnati, OH (US)

(72) Inventors: Robert Wayne Glenn, Jr., Liberty Township, OH (US); Kathleen Mary Kaufman, Cincinnati, OH (US); Dariush Hosseinpour, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days. days.

(21) Appl. No.: 14/739,588

(22) Filed: Jun. 15, 2015

(65) Prior Publication Data
US 2015/0359725 A1    Dec. 17, 2015

Related U.S. Application Data

(60) Provisional application No. 62/012,614, filed on Jun. 16, 2014.

(51) Int. Cl.
*A61Q 5/12* (2006.01)
*A61K 8/898* (2006.01)
*A61K 8/04* (2006.01)
*A61K 8/92* (2006.01)
*A61K 8/31* (2006.01)
*A61K 8/06* (2006.01)

(52) U.S. Cl.
CPC .............. *A61K 8/898* (2013.01); *A61K 8/046* (2013.01); *A61K 8/06* (2013.01); *A61K 8/31* (2013.01); *A61K 8/92* (2013.01); *A61Q 5/12* (2013.01); *A61K 2800/21* (2013.01); *A61K 2800/54* (2013.01)

(58) Field of Classification Search
None
See application file for complete search history.

(56) References Cited

U.S. PATENT DOCUMENTS

| | | |
|---|---|---|
| 3,236,733 A | 2/1966 | Karsten et al. |
| 3,938,708 A | 2/1976 | Burger |
| 4,607,756 A | 8/1986 | Courtman |
| 4,880,618 A | 11/1989 | Grollier et al. |
| 5,012,978 A | 5/1991 | Bolduc |
| 5,077,040 A | 12/1991 | Bergmann et al. |
| 5,674,478 A | 10/1997 | Dodd et al. |
| 5,985,295 A | 11/1999 | Peffly |
| 6,039,036 A | 3/2000 | Restle et al. |
| 6,589,509 B2 | 7/2003 | Keller et al. |
| 6,602,494 B1 | 8/2003 | Jahedshoar et al. |
| 6,604,693 B2 | 8/2003 | Santagiuliana |
| 6,605,577 B1 | 8/2003 | Harrison et al. |
| 6,642,194 B2 | 11/2003 | Harrison et al. |
| 6,656,458 B1 | 12/2003 | Philippe et al. |
| 6,927,196 B2 | 8/2005 | Snyder et al. |
| 7,001,594 B1 | 2/2006 | Peffly et al. |
| 7,217,777 B2 | 5/2007 | Lange et al. |
| 7,316,815 B2 | 1/2008 | Philippe et al. |
| RE40,534 E | 10/2008 | Harrison et al. |
| 7,455,195 B2 | 11/2008 | Mekata |
| 7,462,585 B2 | 12/2008 | Uehara |
| 7,470,651 B2 | 12/2008 | Uehara et al. |
| 7,504,093 B2 | 3/2009 | Bracken et al. |
| 7,759,378 B2 | 7/2010 | Philippe et al. |
| 8,017,106 B2 | 9/2011 | Keller et al. |
| 8,263,053 B2 | 9/2012 | Duvel et al. |
| 8,475,777 B2 | 7/2013 | Rautschek |
| 8,476,472 B2 | 7/2013 | Hojo et al. |
| 8,642,021 B2 | 2/2014 | Brautigam et al. |
| 8,697,040 B2 | 4/2014 | Duvel et al. |
| 8,956,597 B2 | 2/2015 | Gesztesi et al. |
| 8,999,306 B2 | 4/2015 | Duvel et al. |
| 9,255,184 B2 | 2/2016 | Paul |
| 9,308,398 B2 | 4/2016 | Hutton et al. |
| 9,358,186 B2 | 6/2016 | Chandra et al. |
| 9,539,199 B2 | 1/2017 | Beer et al. |
| 9,539,208 B2 | 1/2017 | Tamarkin et al. |
| 9,540,489 B2 | 1/2017 | Panandiker et al. |
| 9,828,170 B2 | 11/2017 | Nomura et al. |
| 2001/0008630 A1 | 7/2001 | Pyles et al. |

(Continued)

FOREIGN PATENT DOCUMENTS

| | | |
|---|---|---|
| DE | 10304721 B4 | 3/2007 |
| EP | 978271 A1 | 2/2000 |

(Continued)

OTHER PUBLICATIONS

In-Cosmetics 2012(Apr. 2012).*
Silsoft *253 (Aug. 2013).*
All Office Actions, U.S. Appl. No. 14/739,670.
All Office Actions, U.S. Appl. No. 14/739,708.
All Office Actions, U.S. Appl. No. 14/739,755.
Carolyn Evans: "Scalp Cleansing, Scalp Tonique, Hair Shampoo, Hair Conditioner, Demonstration" Youtube, Apr. 22, 2012, p. 2. First part of the video (0-3 min) dedicated to "scalp cleansing"; second part of the video (3-6 min) dedicated to the treatment of the hair.

(Continued)

*Primary Examiner* — Jyothsna A Venkat
(74) *Attorney, Agent, or Firm* — Alexandra S. Anoff

(57) ABSTRACT

A method of treating the hair including providing a concentrated hair care composition in an aerosol foam dispenser. The concentrated hair care composition includes one or more silicones, perfume, and less than 10% high melting point fatty compounds. The method also includes dispensing the concentrated hair care composition from the aerosol foam dispenser as a dosage of foam; applying the foam to the hair; and rinsing the foam from the hair. The foam has a density of from about 0.025 g/cm$^3$ to about 0.40 g/cm$^3$ when dispensed from the aerosol foam dispenser.

8 Claims, 4 Drawing Sheets

(56) References Cited

U.S. PATENT DOCUMENTS

| | | |
|---|---|---|
| 2001/0025857 A1 | 10/2001 | Baudin |
| 2002/0031532 A1 | 3/2002 | Uchiyama |
| 2002/0197213 A1* | 12/2002 | Schmenger ............ A61K 8/046 424/47 |
| 2003/0152542 A1 | 8/2003 | Decoster et al. |
| 2003/0228272 A1 | 12/2003 | Amjad et al. |
| 2004/0018164 A1 | 1/2004 | Zofchak et al. |
| 2004/0076595 A1 | 4/2004 | Khan |
| 2004/0229763 A1 | 11/2004 | Hutton, III et al. |
| 2004/0247550 A1 | 12/2004 | Asari et al. |
| 2005/0002892 A1 | 1/2005 | Khan et al. |
| 2005/0136011 A1 | 6/2005 | Nekludoff et al. |
| 2005/0196372 A1 | 9/2005 | Cajan |
| 2005/0196376 A1 | 9/2005 | Loomis |
| 2005/0197421 A1 | 9/2005 | Loomis |
| 2005/0222001 A1 | 10/2005 | Baumeister et al. |
| 2005/0274737 A1 | 12/2005 | Krause et al. |
| 2006/0054634 A1 | 3/2006 | Mekata |
| 2006/0083704 A1 | 4/2006 | Torgerson |
| 2006/0292104 A1 | 12/2006 | Guskey et al. |
| 2006/0293197 A1 | 12/2006 | Uehara et al. |
| 2007/0179207 A1 | 8/2007 | Fernandez de Castro et al. |
| 2007/0286837 A1 | 12/2007 | Torgerson |
| 2008/0066773 A1 | 3/2008 | Anderson et al. |
| 2008/0138296 A1 | 6/2008 | Tamarkin et al. |
| 2008/0292560 A1 | 11/2008 | Tamarkin et al. |
| 2008/0292574 A1 | 11/2008 | Uehara |
| 2009/0041706 A1 | 2/2009 | Molenda et al. |
| 2009/0232759 A1 | 9/2009 | Bell et al. |
| 2010/0092405 A1 | 4/2010 | Philippe et al. |
| 2010/0143280 A1 | 6/2010 | Yokogi et al. |
| 2010/0143281 A1 | 6/2010 | Okada et al. |
| 2010/0143282 A1 | 6/2010 | Yokogi et al. |
| 2010/0143425 A1 | 6/2010 | Okada et al. |
| 2010/0178265 A1 | 7/2010 | Molenda et al. |
| 2011/0135588 A1* | 6/2011 | Uehara ............... A61K 8/42 424/70.12 |
| 2011/0226273 A1 | 9/2011 | Deardorff et al. |
| 2011/0280110 A1 | 11/2011 | Chen |
| 2011/0318295 A1 | 12/2011 | Shimizu |
| 2012/0020908 A1 | 1/2012 | Paul |
| 2012/0043352 A1 | 2/2012 | Rasmussen et al. |
| 2012/0114819 A1 | 5/2012 | Ragnarsson |
| 2012/0171147 A1 | 7/2012 | Rautschek |
| 2012/0288465 A1 | 11/2012 | Loechel |
| 2013/0075430 A1 | 3/2013 | Ragnarsson |
| 2013/0202666 A1 | 8/2013 | Petkov et al. |
| 2013/0280192 A1 | 10/2013 | Carter et al. |
| 2013/0284196 A1 | 10/2013 | Murdock et al. |
| 2014/0105943 A1 | 4/2014 | Pistoria et al. |
| 2014/0107224 A1 | 4/2014 | Osman et al. |
| 2014/0116458 A1* | 5/2014 | Krueger ............... A61Q 5/12 132/202 |
| 2014/0135414 A1 | 5/2014 | Loomis |
| 2014/0237732 A1 | 8/2014 | Zuedel Fernandes et al. |
| 2014/0261517 A1 | 9/2014 | Humphreys et al. |
| 2014/0302103 A1 | 10/2014 | Carter et al. |
| 2014/0356303 A1 | 12/2014 | Rocco et al. |
| 2014/0377206 A1 | 12/2014 | Uehara et al. |
| 2015/0011450 A1 | 1/2015 | Carter et al. |
| 2015/0030643 A1 | 1/2015 | Gartstein et al. |
| 2015/0093420 A1 | 4/2015 | Snyder et al. |
| 2015/0190326 A1 | 7/2015 | Brouard et al. |
| 2015/0359725 A1 | 12/2015 | Glenn, Jr. et al. |
| 2015/0359726 A1 | 12/2015 | Glenn, Jr. et al. |
| 2015/0359727 A1 | 12/2015 | Glenn, Jr. et al. |
| 2015/0359728 A1 | 12/2015 | Glenn, Jr. et al. |
| 2016/0000673 A1 | 1/2016 | Ainger et al. |
| 2016/0310375 A1 | 4/2016 | Torres Rivera et al. |
| 2016/0310376 A1 | 4/2016 | Torres Rivera et al. |
| 2016/0143821 A1 | 5/2016 | Chang et al. |
| 2016/0309871 A1 | 10/2016 | Torres Rivera et al. |
| 2016/0310371 A1 | 10/2016 | Zhao et al. |
| 2016/0310372 A1 | 10/2016 | Glenn, Jr. et al. |
| 2016/0310377 A1 | 10/2016 | Torres Rivera et al. |
| 2016/0310397 A1 | 10/2016 | Johnson et al. |
| 2017/0087068 A1 | 3/2017 | Callens et al. |
| 2017/0165155 A1 | 6/2017 | Glenn, Jr. et al. |
| 2017/0165156 A1 | 6/2017 | Glenn, Jr. et al. |
| 2017/0165157 A1 | 6/2017 | Glenn, Jr. et al. |
| 2017/0165162 A1 | 6/2017 | Glenn, Jr. et al. |
| 2017/0165163 A1 | 6/2017 | Glenn, Jr. et al. |
| 2017/0165191 A1 | 6/2017 | Glenn, Jr. et al. |
| 2017/0174413 A1 | 6/2017 | Callens et al. |
| 2017/0304184 A1 | 10/2017 | Glenn, Jr. et al. |
| 2017/0304185 A1 | 10/2017 | Glenn, Jr. et al. |
| 2017/0304186 A1 | 10/2017 | Glenn, Jr. et al. |

FOREIGN PATENT DOCUMENTS

| | | |
|---|---|---|
| EP | 2138155 A2 | 12/2009 |
| EP | 2883533 A1 | 6/2015 |
| JP | 3242689 B2 | 12/2001 |
| JP | 2003-119113 A | 4/2003 |
| JP | 2010-132569 A | 6/2010 |
| JP | 4694171 B2 | 6/2011 |
| JP | 2014-125477 A | 7/2014 |
| WO | WO 96/19188 A1 | 6/1996 |
| WO | WO 97/20626 A1 | 6/1997 |
| WO | WO0222085 A1 | 3/2002 |
| WO | WO 2004/078901 A1 | 9/2004 |
| WO | WO 2013/176666 A1 | 11/2013 |

OTHER PUBLICATIONS

Anonymous: "GNPD—Anti-Dandruff Shampoo", Nov. 1, 2012.
Anonymous "Shampoo only Scalp? or entire head?—The Long Hair Community Discussion Boards", Feb. 1, 2011, Retrieved from the internet: URL: http://forums.longhaircommunity.com/archieve/index.php/t-91788.html, retrieved on Jul. 21, 2016.
Samantha Zabell: "Mistakes You're Making Washing Your Hair—How You're Washing Your Hair Wrong", Jan. 14, 2014, Retrieved from the Internet: URL: http://www.goodhousekeeping.com/beauty/hair/tips/a19894/mistakes-washing-your-hair/, Section 3. "Overdoing it on shampoo and/or conditioner"; p. 2, retrieved on Jul. 21, 2016.
Anonymous: "GNPD—Anti-Dandruff Shampoo + Conditioner Set", Procter and Gamble China, Apr. 1, 2009, Mintel GNPD, Retrieved from the Internet: URL: http://www.gnpd.com/sinatra/recordpage/107827/from_search/EkXVQ1u6vF/?page=2, Retrieved on Jul. 12, 2016.
Database GNPD, Mintel; Aug. 2014 "Gold Olive Haircare Set".
Database GNPD Mintel; May 2014, "Coconut & Macadamia Oil Nourishing Shampoo and Nourishing Conditioner".
"Clarifying Shampoo", Mintel, Jun. 2015.
"Reinforcing conditioner", Mintel, May 2014.
PCT International Search Report and Written Opinion for PCT/US2016/066753 dated Feb. 28, 2017, 11 pages.
PCT International Search Report and Written Opinion for PCT/US2016/067916 dated Mar. 29, 2016.
PCT International Search Report and Written Opinion for PCT/US2016/028731 dated Jul. 5, 2016, 11 pages.
PCT International Search Report and Written Opinion for PCT/US2016/028860 dated Jul. 7, 2016, 11 pages.
PCT International Search Report and Written Opinion for PCT/US2015/035796 dated Sep. 14, 2015, 9 pages.
PCT International Search Report and Written Opinion for PCT/US2015/035756 dated Dec. 21, 2015, 13 pages.
PCT International Search Report and Written Opinion for PCT/US2015/035797 dated Sep. 14, 2015, 9 pages.
PCT International Search Report and Written Opinion for PCT/US2015/035799 dated Sep. 14, 2015, 9 pages.
PCT International Search Report and Written Opinion for PCT/US2016/028739 dated Jul. 4, 2016, 11 pages.
PCT International Search Report and Written Opinion for PCT/US2016/066755 dated Feb. 27, 2017, 12 pages.
PCT International Search Report and Written Opinion for PCT/US2016/066759 dated Feb. 27, 2017, 11 pages.
PCT International Search Report and Written Opinion for PCT/US2016/066754 dated Feb. 20, 2017, 11 pages.

(56) References Cited

OTHER PUBLICATIONS

PCT International Search Report and Written Opinion for PCT/US2016/028745 dated Aug. 8, 2016.
PCT International Search Report and Written Opinion for PCT/US2016/028853 dated Sep. 30, 2016, 19 pages.
PCT International Search Report and Written Opinion for PCT/US2016/028855, dated Oct. 5, 2016, 18 pages.
PCT International Search Report and Written Opinion for PCT/US2016/028743 dated Jul. 25, 2016.
U.S. Appl. No. 15/380,194, filed Dec. 15, 2016, Glenn, Jr. et al.
U.S. Appl. No. 15/380,218, filed Dec. 15, 2016, Glenn, Jr. et al.
U.S. Appl. No. 15/380,261, filed Dec. 15, 2016, Glenn, Jr. et al.
U.S. Appl. No. 15/380,293, filed Dec. 15, 2016, Glenn, Jr. et al.
U.S. Appl. No. 15/380,345, filed Dec. 15, 2016, Glenn, Jr. et al.
U.S. Appl. No. 15/380,373, filed Dec. 15, 2016, Glenn, Jr. et al.
U.S. Appl. No. 15/492,429, filed Apr. 20, 2017, Glenn, Jr. et al.
U.S. Appl. No. 15/492,451, filed Apr. 20, 2017, Glenn, Jr. et al.
U.S. Appl. No. 15/492,469, filed Apr. 20, 2017, Glenn, Jr. et al.
U.S. Appl. No. 15/381,298, filed Dec. 16, 2016, Callens et al.
All final and non-final office actions for U.S. Appl. No. 15/843,069.
All final and non-final office actions for U.S. Appl. No. 15/843,146.
All final and non-final office actions for U.S. Appl. No. 15/843,178.
Fabida. https://makeupandbeauty.com/head-shoulders-anti-dandruff-itchy-scalp-care-shampoo-review/. Published Jun. 26, 2012.
Free Sample. https://web.archive.org/web/20111116042029/http://freesampleprincess.com/head-and-shoulders-itchy-scalp-care-free-sample. Published Nov. 16, 2011.
Hair Conditioner Tips and Tricks. https://web.archive.org/web/20121106125731/http://www.thehairstyler.com/features/articles/hair-care/hair-conditioner-tips-and-tricks. Published Nov. 6, 2012.
Mommy Story, http://www.amommystory.com/2011/11/head-shoulders-eucalyptus-itchy-scalp-care-to-the-rescue-review-give-away.html. Published Nov. 21, 2011.
PCT International Search Report and Written Opinion for PCT/US2017/028472 dated Jun. 29, 2017.
PCT International Search Report and Written Opinion for PCT/US2017/028473 dated Jun. 29, 2017.
PCT International Search Report and Written Opinion for PCT/US2017/028474 dated Jun. 29, 2017.
Stylecaster. http://stylecaster.com/beauty/how-to-get-rid-of-dandruff/. Published: Jan. 16, 2014.
U.S. Appl. No. 15/843,069, filed Dec. 15, 2017, Glenn, Jr. et al.
U.S. Appl. No. 15/843,146, filed Dec. 15, 2017, Glenn, Jr. et al.
U.S. Appl. No. 15/843,178, filed Dec. 15, 2017, Glenn, Jr. et al.

\* cited by examiner

METHOD OF TREATING HAIR WITH A CONCENTRATED CONDITIONER

FIELD OF THE INVENTION

Described herein is a method of treating hair with a concentrated hair conditioning composition provided in an aerosol foam dispenser.

BACKGROUND OF THE INVENTION

Today's hair conditioners almost universally comprise high levels of high melting point fatty compounds, the most common of which are C16 to C18 fatty alcohols. These high melting point fatty compounds are employed as structuring agents wherein they are combined with one or more surfactants and an aqueous carrier to form a gel network. The gel network provides a viscous and high yield point rheology which facilitates the dispensing of the conditioner from a bottle or tube and the subsequent distribution and spreading of the product through the hair by the consumer. The gel network structuring also enables incorporation of silicones, perfumes and oils in the form of an oil-in-water emulsion that is phase stable. These silicones and oils are intended to be deposited on the hair to provide the primary hair conditioning benefits including wet and dry combing friction reduction and hair manageability etc.

However, today's gel network hair conditioners lead to excessive co-deposits of the high melting point fatty compound on the hair over multiple cycles. Additionally, the deposited high melting point fatty compounds build-up on hair over multiple cycles and lead to significant waxy build-up on hair and hair weigh down. Indeed, one of the major consumer complaints with hair conditioners is waxy residue which makes hair look greasy or feel heavy. Many current gel network hair conditioners deposit up to 10 times more high melting point fatty compounds (fatty alcohols) than silicone or oil after approximately 10 treatment cycles in technical testing. While not being bound to theory, this is hypothesized to be due to the ~10× greater concentration of high melting point weight fatty compounds in the product relative to the silicone or oil. Such a high level of melting point fatty compounds (fatty alcohols) may be required to produce a shelf stable gel network with sufficient structuring for consumer acceptable viscosity and rheology.

Described herein is a concentrated hair care composition that enables new product opportunities and consumer benefits by addressing the current disadvantages associated with gel network conditioners. Is has been found that concentrated and ultra-low viscosity hair conditioner compositions can be delivered to the hair in foamed form. These new concentrated silicone nanoemulsion compositions enable sufficient dosage from a foam delivery form while also eliminating the need for high melting point fatty compounds or other "insoluble" structurants that can lead to significant co-deposits, build-up and weigh down of hair. The net result has been a step change improvement in silicone deposition purity versus today's rinse-off products and an improvement in technical performance benefits from such a pure and transparent deposited silicone layer. These benefits include multicycle hair conditioning without hair weigh down, durable conditioning, reduced hair dye fade, and increased color vibrancy.

Nanoemulsion technology development is hindered by complex stability issues that emerge when droplet sizes are driven to the nanoscale. This may be especially problematic in the presence of higher levels of perfume oils which may be required for such a concentrated product. The concentrated hair care composition described herein is therefor also focused on improved stability.

SUMMARY OF THE INVENTION

Described herein is a method of treating the hair, the method comprising (1) providing a concentrated hair care composition in an aerosol foam dispenser, wherein the concentrated hair care composition comprises (a) from about 3% to about 22% of one or more silicones, by weight of the concentrated hair care composition, wherein the particle size of the one or more silicones is from about 1 nm to about 300 nm; (b) less than 10% high melting point fatty compounds, by weight of the concentrated hair care composition; (c) from about 1% to about 12% propellant, by weight of the concentrated hair care composition; (d) from about 0.5% to about 7% perfume, by weight of the concentrated hair care composition; and (e) from about 75% to about 95% water, and in one embodiment from about 60% to about 90% water, by weight of the concentrated hair care composition; wherein the concentrated hair care composition has a liquid phase viscosity of from about 1 centipoise to about 15,000 centipoise; wherein the concentrated hair care composition has silicone to high melting point fatty compound ratio of from about 100:0 to about 50:50; and wherein the concentrated hair care composition has a silicone to perfume ratio of from about 98:2 to about 50:50; (2) dispensing the concentrated hair care composition from the aerosol foam dispenser as a foam; (3) applying the foam to the hair; and (4) rinsing the foam from the hair; wherein the foam has a density of from about 0.025 g/cm$^3$ to about 0.15 g/cm$^3$, and alternatively from about 0.025 g/cm$^3$ to about 0.30 g/cm$^3$, when dispensed from the aerosol foam dispenser.

Also described herein is an aerosol foam dispenser comprising a concentrated hair care composition, the concentrated hair care composition comprising (1) from about 3% to about 22% of an oil, by weight of the concentrated hair care composition, wherein the particle size of the oil is from about 1 nm to about 300 nm; (2) less than 10% high melting point fatty compounds, by weight of the concentrated hair care composition; (3) from about 1% to about 12% propellant; (4) from about 0.5% to about 7% perfume, by weight of the concentrated hair care composition; and (5) from about 75% to about 95% water, and in an embodiment from about 60% to about 90% water, by weight of the concentrated hair care composition; wherein the concentrated hair care composition has a liquid phase viscosity of from about 1 centipoise to about 15,000 centipoise; wherein the concentrated hair care composition has silicone to high melting point fatty compound ratio of from about 100:0 to about 50:50; wherein the concentrated hair care composition has a silicone to perfume ratio of from about 98:2 to about 50:50; wherein the foam has a density of from about 0.025 g/cm$^3$ to about 0.15 g/cm$^3$, and alternatively from about 0.025 g/cm$^3$ to about 0.40 g/cm$^3$, when dispensed from the aerosol foam dispenser; and wherein the concentrated hair care composition is rinse-off.

BRIEF DESCRIPTION OF THE DRAWINGS

While the specification concludes with claims, it is believed that the same will be better understood from the following description taken in conjunction with the accompanying drawings in which:

DETAILED DESCRIPTION OF THE INVENTION

Figure 1:
FIG. 1 is an SEM image of hair treated with a Pantene Clarifying Shampoo plus a Pantene Anti-breakage Conditioner.

While the specification concludes with claims particularly pointing out and distinctly claiming the invention, it is believed that the present invention will be better understood from the following description.

As used herein, the articles including "a" and "an" when used in a claim, are understood to mean one or more of what is claimed or described.

As used herein, "comprising" means that other steps and other ingredients which do not affect the end result can be added. This term encompasses the terms "consisting of" and "consisting essentially of".

As used herein, "mixtures" is meant to include a simple combination of materials and any compounds that may result from their combination.

As used herein, "molecular weight" or "M.Wt." refers to the weight average molecular weight unless otherwise stated.

As used herein, the terms "include," "includes," and "including," are meant to be non-limiting and are understood to mean "comprise," "comprises," and "comprising," respectively.

As used herein, the term "concentrated" means a hair care composition comprising from about 5% to about 22% of one or more silicones, by weight of the hair care composition.

As used herein, the term "nanoemulsion" means an oil-in-water (o/w) emulsion with an average particle size ranging from about 1 nm to about 100 nm. The particle size referred to herein is z-average measured by dynamic light scattering. The nanoemulsion described herein may be prepared by the following methods: (1) mechanically breaking down the emulsion droplet size; (2) spontaneously forming the emulsion (may be referred to as a microemulsion in the literature); and (3) using emulsion polymerization to achieve average particle size in the target range described herein.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Hair Care Composition

The method of treating the hair described herein comprises providing a concentrated hair care composition in an aerosol foam dispenser. The concentrated hair care composition may comprise one or more silicones and perfume.

A. Silicone Deposition Purity

The method of treating hair comprises dispensing the concentrated hair care composition described herein from the aerosol foam dispenser as a dosage of foam. The foam may comprise a silicone deposition purity of from about 40% to about 100%, alternatively from about 50% to about 100%, alternatively from about 60% to about 100%, alternatively from about 70% to about 100%, and alternatively from about 80% to about 100%, after applying the foam to the hair and rinsing the foam from the hair.

Deposition Purity is determined by the ratio of silicone deposited per weight of hair to the total deposition of other ingredients per weight of hair. Silicone is determined by either extraction or digestion of the hair followed by an analysis with a quantitative elemental technique such as ICP for total silicon and converting to silicone based on the % of silicon in the silicone by weight. The total deposition may be determined by the sum of separate deposition measurements or by a Single Inclusive Measurement of total deposition. The separate deposition measurements may include but are not limited to: fatty alcohols, EGDS, quaternized agents and silicone. Typically these measurements involve extracting the hair then separating the ingredients of interest with chromatography and quantifying with an externally calibration based on test solution concentration. The Single Inclusive Measurement of total deposition is gravimetric. The hair is thoroughly extracted and the residue determined by weighing the dissolved residue in the extract after evaporating the solvent. This residue contains both deposited ingredients and naturally occurring extractable compounds from the hair (primarily lipids). The naturally occurring extractable compounds are quantified and subtracted from the total. These include: fatty acids, squalene, cholesterol, ceramides, wax esters, triglycerides and sterol esters. The method of quantitation is similar to the deposition measurements. Other supporting evidence of Deposition Purity may include spectroscopic or topography mapping of the hair surface.

B. Silicones

The concentrated hair care composition may comprise from about 5% to about 20%, alternatively from about 8% to about 18%, and alternatively from about 10% to about 14% of one or more silicones, by weight of the concentrated hair care composition. In a further embodiment, the hair care composition may comprise from about 3% to about 25%, alternatively from about 4% to about 20%, alternatively from about 5% to about 15% of one or more silicones, and alternatively from about 6% to about 12% by weight of the concentrated hair care composition. The particle size of the one or more silicones may be from about 1 nm to about 100 nm, alternatively from about 5 nm to about 80 nm, alternatively from about 10 nm to about 60 nm, and alternatively from about 12 nm to about 50 nm. In a further embodiment, the particle size of the one or more silicones may be from about 1 nm to about 500 nm, alternatively from about 5 nm to about 300 nm, alternatively from about 8 nm to about 200 nm, and alternatively from about 10 nm to about 100 nm.

The particle size of the one or more silicones may be measured by dynamic light scattering (DLS). A Malvern Zetasizer Nano ZEN3600 system (www.malvern.com) using He—Ne laser 633 nm may be used for the measurement at 25° C. Prior low level centrifugation may be required on opaque formulas comprising larger insoluble structures (e.g., fatty alcohols) that would need to be isolated from the emulsion particles.

The autocorrelation function may be analyzed using the Zetasizer Software provided by Malvern Instruments, which determines the effective hydrodynamic radius, using the Stokes-Einstein equation:

$$D = \frac{k_B T}{6\pi\eta R}$$

wherein $k_B$ is the Boltzmann Constant, T is the absolute temperature, $\eta$ is the viscosity of the medium, D is the mean diffusion coefficient of the scattering species, and R is the hydrodynamic radius of particles.

Particle size (i.e. hydrodynamic radius) may be obtained by correlating the observed speckle pattern that arises due to Brownian motion and solving the Stokes-Einstein equation, which relates the particle size to the measured diffusion constant, as is known in the art.

Other methods known in the art may also be employed to measure particle size including cryo-SEM, cryo-TEM, and lazer-diffraction methods.

For each sample, 3 measurements may be made and Z-average values may be reported as the particle size.

In an embodiment, the one or more silicones may be in the form of a nanoemulsion. A nanoemulsion, as defined herein, is an emulsion wherein the particle size is below 100 nm. The nanoemulsion may comprise any silicone suitable for application to the skin and/or hair. In one embodiment, from about 25% to about 100% of the one or more silicones is in the form of a nanoemulsion, in another embodiment from about 50% to about 100% of the one or more silicones is in the form of a nanoemulsion, and in another embodiment from about 75% to about 100% of the one or more silicones is in the form of a nanoemulsion.

In an embodiment, the one or more silicones may include in their molecular structure polar functional groups such as Si—OH (present in dimethiconols), primary amines, secondary amines, tertiary amines, and quaternary ammonium salts. The one or more silicones may be selected from the group consisting of aminosilicones, pendant quaternary ammonium silicones, terminal quaternary ammonium silicones, amino polyalkylene oxide silicones, quaternary ammonium polyalkylene oxide silicones, and amino morpholino silicones.

The one or more silicones may comprise:
(a) at least one aminosilicone corresponding to formula (V):

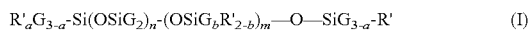
(I)

in which:
G is chosen from a hydrogen atom, a phenyl group, OH group, and $C_1$-$C_8$ alkyl groups, for example methyl,
a is an integer ranging from 0 to 3, and in one embodiment a is 0,
b is chosen from 0 and 1, and in one embodiment b is 1, m and n are numbers such that the sum (n+m) can range for example from 1 to 2 000, such as for example from 50 to 150, wherein n can be for example chosen from numbers ranging from 0 to 1 999, such as for example from 49 to 149, and wherein m can be chosen from numbers ranging for example from 1 to 2 000, such as for example from 1 to 10;
R' is a monovalent group of formula —$C_qH_{2q}$L in which q is a number from 2 to 8 and L is an optionally quaternized amine group chosen from the groups:
—NR"—$CH_2$—$CH_2$—N'($R^1$)$_2$,
—N(R")$_2$,
—$N^+$(R")$_3$A$^-$,
—$N^+$H(R")$_2$A$^-$,
—$N^+$H$_2$(R")A$^-$, and
—N(R")—$CH_2$—$CH_2$—$N^+$R"H$_2$A$^-$,
in which R' can be chosen from a hydrogen atom, phenyl groups, benzyl groups, and saturated monovalent hydrocarbon-based groups, such as for example an alkyl group comprising from 1 to 20 carbon atoms, and A$^-$ is chosen from halide ions such as, for example, fluoride, chloride, bromide and iodide.

In an embodiment, the one or more silicones may include those corresponding to formula (1) wherein a=0, G=methyl, m and n are numbers such that the sum (n+m) can range for example from 1 to 2 000, such as for example from 50 to 150, wherein n can be for example chosen from numbers ranging from 0 to 1 999, such as for example from 49 to 149, and wherein m can be chosen from numbers ranging for example from 1 to 2 000, such as for example from 1 to 10; and L is —N($CH_3$)$_2$ or —$NH_2$, alternatively —$NH_2$.

Additional said at least one aminosilicone of the invention include:
(b) pendant quaternary ammonium silicones of formula (VII):

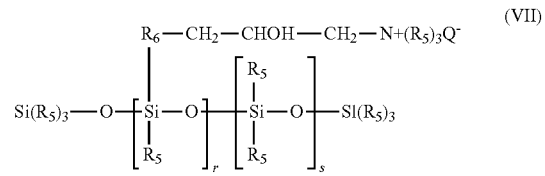

in which:
$R_5$ is chosen from monovalent hydrocarbon-based groups comprising from 1 to 18 carbon atoms, such as $C_1$-$C_{18}$ alkyl groups and $C_2$-$C_{18}$ alkenyl groups, for example methyl;
$R_6$ is chosen from divalent hydrocarbon-based groups, such as divalent $C_1$-$C_{18}$ alkylene groups and divalent $C_1$-$C_{18}$ alkylenoxy groups, for example $C_1$-$C_8$ alkylenoxy groups, wherein said $R_6$ is bonded to the Si by way of an SiC bond;
$Q^-$ is an anion that can be for example chosen from halide ions, such as chloride, and organic acid salts (such as acetate);
r is an average statistical value ranging from 2 to 20, such as from 2 to 8;
s is an average statistical value ranging from 20 to 200, such as from 20 to 50.

Such aminosilicones are described more particularly in U.S. Pat. No. 4,185,087, the disclosure of which is incorporated by reference herein.

A silicone which falls within this class is the silicone sold by the company Union Carbide under the name "Ucar Silicone ALE 56".

Further examples of said at least one aminosilicone include:
c) quaternary ammonium silicones of formula (VIIb):

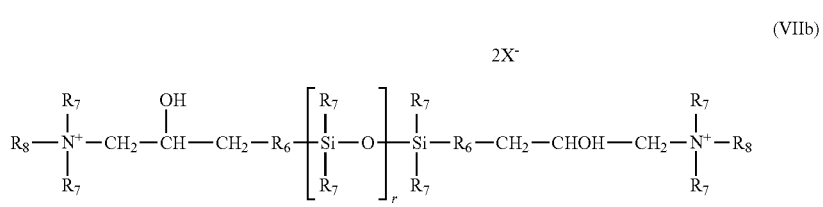

(VIIb)

in which:

groups $R_7$, which may be identical or different, are each chosen from monovalent hydrocarbon-based groups comprising from 1 to 18 carbon atoms, such as $C_1$-$C_{18}$ alkyl groups, for example methyl, $C_2$-$C_{18}$ alkenyl groups, and rings comprising 5 or 6 carbon atoms;

$R_6$ is chosen from divalent hydrocarbon-based groups, such as divalent $C_1$-$C_{18}$ alkylene groups and divalent $C_1$-$C_{18}$ alkylenoxy, for example $C_1$-$C_8$, group connected to the Si by an SiC bond;

$R_8$, which may be identical or different, represent a hydrogen atom, a monovalent hydrocarbon-based group comprising from 1 to 18 carbon atoms, and in particular a $C_1$-$C_{18}$ alkyl group, a $C_2$-$C_{18}$ alkenyl group or a group —$R_6$—NHCOR$_7$;

$X^-$ is an anion such as a halide ion, in particular chloride, or an organic acid salt (acetate, etc.); r represents an average statistical value from 2 to 200 and in particular from 5 to 100.

Such silicones are described, for example, in application EP-A-0 530 974, the disclosure of which is incorporated by reference herein.

Silicones falling within this class are the silicones sold by the company Goldschmidt under the names Abil Quat 3270, Abil Quat 3272 and Abil Quat 3474.

Further examples of said at least one aminosilicone include:
d) quaternary ammonium and polyalkylene oxide silicones wherein the quaternary nitrogen groups are located in the polysiloxane backbone, at the termini, or both.

Such silicones are described in PCT Publication No. WO 2002/010257, the disclosure of which is incorporated by reference herein.

Silicones falling within this class are the silicones sold by the company Momentive under the names Silsoft Q . . . .

(e) Aminofunctional silicones having morpholino groups of formula (V):

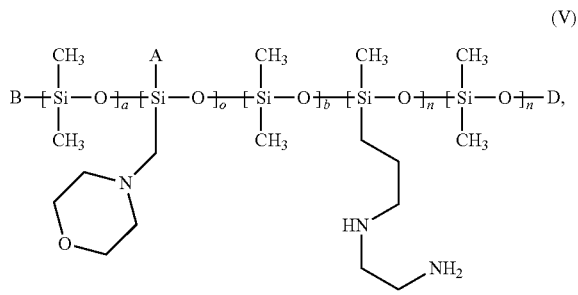

(V)

in which

A denotes a structural unit (I), (II), or (III) bound via —O—

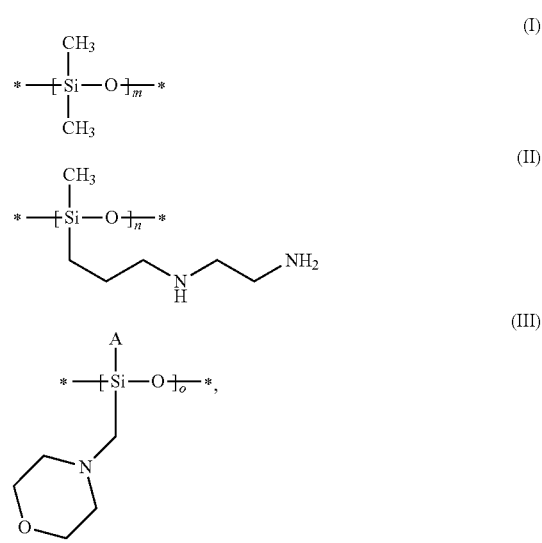

or an oligomeric or polymeric residue, bound via —O—, containing structural units of formulas (I), (II), or (III), or half of a connecting oxygen atom to a structural unit (III), or denotes —OH, \* denotes a bond to one of the structural units (I), (II), or (III), or denotes a terminal group B (Si-bound) or D (O-bound), B denotes an —OH, —O—Si(CH$_3$)$_3$, —O—Si(CH$_3$)$_2$OH, —O—Si(CH$_3$)$_2$OCH$_3$ group, D denotes an —H, —Si(CH$_3$)$_3$, —Si(CH$_3$)$_2$OH, —Si(CH$_3$)$_2$OCH$_3$ group, a, b, and c denote integers between 0 and 1000, with the provision that a+b+c>0, m, n, and o denote integers between 1 and 1000.

Aminofunctional silicones of this kind bear the INCI name:

Amodimethicone/Morpholinomethyl Silsesquioxane Copolymer. A particularly suitable amodimethicone is the product having the commercial name Wacker Belsil® ADM 8301E.

Examples of such silicones are available from the following suppliers:
offered by the company Dow Corning:
Fluids: 2-8566, AP 6087, AP 6088, DC 8040 Fluid, fluid 8822A DC, DC 8803 & 8813 polymer, 7-6030, AP-8104, AP 8201;
Emulsions: CE-8170 AF Micro Emulsion, 2-8177, 2-8194 Microemulsion, 9224 Emulsion, 939, 949, 959, DC 5-7113 Quat Microemulsion, DC 5-7070

Emulsion, DC CE-8810, CE 8401 Emulsion, CE 1619, Dow Corning Toray SS-3551, Dow Corning Toray SS-3552;

offered by the company Wacker:
Wacker Belsil ADM 652, ADM 656, 1100, 1600, 1650 (fluids) ADM 6060 (linear amodimethicone) emulsion; ADM 6057 E (branched amodimethicone) emulsion; ADM 8020 VP (micro emulsion); SLM 28040 (micro emulsion);

offered by the Company Momentive:
Silsoft 331, SF1708, SME 253 & 254 (emulsion), SM2125 (emulsion), SM 2658 (emulsion), Silsoft Q (emulsion)

offered by the company Shin-Etsu:
KF-889, KF-867S, KF-8004, X-52-2265 (emulsion);

offered by the Company Siltech Silicones:
Siltech E-2145, E-Siltech 2145-35;

offered by the company Evonik Industries:
Abil T Quat 60th

Some non-limiting examples of aminosilicones include the compounds having the following INCI names: Silicone Quaternium-1, Silicone Quaternium-2, Silicone Quaternium-3, Silicone Quaternium-4, Silicone Quaternium-5, Silicone Quaternium-6, Silicone Quaternium-7, Silicone Quaternium-8, Silicone Quaternium-9, Silicone Quaternium-10, Silicone Quaternium-11, Silicone Quaternium-12, Silicone Quaternium-15, Silicone Quaternium-16, Silicone Quaternium-17, Silicone Quaternium-18, Silicone Quaternium-20, Silicone Quaternium-21, Silicone Quaternium-22, Quaternium-80, as well as Silicone Quaternium-2 Panthenol Succinate and Silicone Quaternium-16/Glycidyl Dimethicone Crosspolymer.

In an embodiment, the aminosilicones can be supplied in the form of a nanoemulsion and include MEM 9049, MEM 8177, MEM 0959, MEM 8194, SME 253, and Silsoft Q.

In an embodiment, the one or more silicones may include dimethicones, and/or dimethiconols. The dimethiconols are hydroxyl terminated dimethylsilicones represented by the general chemical formulas

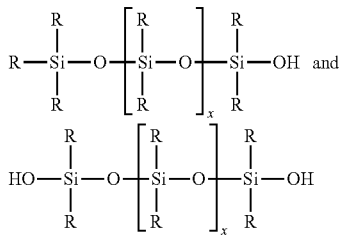

wherein R is an alkyl group (R may be methyl or ethyl) and x is an integer up to about 500, chosen to achieve the desired molecular weight. Commercial dimethiconols typically are sold as mixtures with dimethicone or cyclomethicone (e.g., Dow Corning® 1401, 1402, and 1403 fluids).

C. Nonionic Emulsifiers

The concentrated hair care composition may comprise from about 3% to about 20%, alternatively from about 5% to about 15%, and alternatively from about 7.5% to about 12% of a nonionic emulsifier, by weight of the concentrated hair care composition. In an embodiment, the concentrated hair care composition may comprise from about 0% to about 20%, alternatively from about 0.01% to about 20%, alternatively from about 1% to about 15%, alternatively from about 2% to about 12%, alternatively from about 3% to about 10%, and alternatively from about 4% to about 8% of a nonionic emulsifier, by weight of the concentrated hair care composition. Nonionic emulsifiers may be broadly defined as including compounds containing an alkylene oxide groups (hydrophilic in nature) with a hydrophobic compound, which may be aliphatic or alkyl aromatic in nature. Examples of nonionic emulsifiers include:

1. Alcohol ethoxylates which are condensation products of aliphatic alcohols having from about 8 to about 18 carbon atoms, in either straight chain or branched chain configuration, with from about 2 to about 35 moles of ethylene oxide, e.g., a coconut alcohol ethylene oxide condensate having from about 2 to about 30 moles of ethylene oxide per mole of coconut alcohol, the coconut alcohol fraction having from about 10 to about 14 carbon atom.

2. The polyethylene oxide condensates of alkyl phenols, e.g., the condensation products of the alkyl phenols having an alkyl group containing from about 6 to about 20 carbon atoms in either a straight chain or branched chain configuration, with ethylene oxide, the said ethylene oxide being present in amounts equal to from about 3 to about 60 moles of ethylene oxide per mole of alkyl phenol.

3. Those derived from the condensation of ethylene oxide with the product resulting from the reaction of propylene oxide and ethylene diamine products.

4. Long chain tertiary amine oxides such as those corresponding to the following general formula: R1 R2 R3 N→O wherein R1 contains an alkyl, alkenyl or monohydroxy alkyl redical of from about 8 to about 18 carbon atoms, from 0 to about 10 ethylene oxide moieties, and from 0 to about 1 glyceryl moiety, and R2 and R3 contain from about 1 to about 3 carbon atoms and from 0 to about 1 hydroxy group, e.g., methyl, ethyl, propyl, hydroxyethyl, or hydroxypropyl radicals (the arrow in the formula represents a semipolar bond).

5. Long chain tertiary phosphine oxides corresponding to the following general formula: RR'R"P→O wherein R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R' are each alkyl or monohydroxyalkyl groups containing from about 1 to about 3 carbon atoms. The arrow in the formula represents a semipolar bond.

6. Long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety.

7. Polysorbates, e.g., sucrose esters of fatty acids. Such materials are described in U.S. Pat. No. 3,480,616. e.g., sucrose cocoate (a mixture of sucrose esters of a coconut acid, consisting primarily of monoesters, and sold under the tradenames GRILLOTEN LSE 87K from RITA, and CRODESTA SL-40 from Croda).

8. Alkyl polysaccharide nonionic emulsifiers are disclosed in U.S. Pat. No. 4,565,647, Llenado, issued Jan. 21, 1986, having a hydrophobic group containing from about 6 to about 30 carbon atoms, alternatively from about 10 to about 16 carbon atoms and a polysaccharide, e.g., a polyglycoside, hydrophilic group. The polysaccharide can contain from about 1.0 to about 10, alternatively from about 1.3 to about 3, and alternatively from about 1.3 to about 2.7 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactoside as opposed to a glucoside or galactoside.) The intersaccharide bonds can be, e.g., between the one position of the additional saccharide units and the 2-, 3-, 4-, and/or 6-positions on the preceding saccharide units. Optionally there can be a polyalkyleneoxide chain joining the hydrophobic moiety and the polysaccharide moiety. The alkyl group may contain up to about 3 hydroxy groups and/or the polyalkyleneoxide chain can contain up to about 10, alternatively less than 5, alkylene moieties. Suitable alkyl polysaccharides are octyl, nonyldecyl, undecyldodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses and/or galactoses.

9. Polyethylene glycol (PEG) glyceryl fatty esters, as depicted by the formula RC(O)OCH2 CH(OH)CH2 (OCH2 CH2)n OH wherein n is from about 5 to about 200, alternatively from about 20 to about 100, alternatively from about 30 to about 85, and RC(O)— is an ester wherein R comprises an aliphatic radical having from about 7 to 19 carbon atoms, alternatively from about 9 to 17 carbon atoms, alternatively from about 11 to 17 carbon atoms, alternatively from about 11 to 14 carbon atoms. In an embodiment, the combinations of n may be from about 20 to about 100, with C12-C18, alternatively C12-C15 fatty esters, for minimized adverse effect on foaming.

In an embodiment, the nonionic emulsifier may be a silicone emulsifier. A wide variety of silicone emulsifiers may be useful herein. These silicone emulsifiers are typically organically modified siloxanes, also known to those skilled in the art as silicone surfactants. Useful silicone emulsifiers include dimethicone copolyols. These materials are polydimethyl siloxanes which have been modified to include polyether side chains such as polyethylene oxide chains, polypropylene oxide chains, mixtures of these chains, and polyether chains containing moieties derived from both ethylene oxide and propylene oxide. Other examples include alkyl-modified dimethicone copolyols, i.e., compounds which contain C2-C30 pendant side chains. Still other useful dimethicone copolyols include materials having various cationic, anionic, amphoteric, and zwitterionic pendant moieties.

In an embodiment, the nonionic emulsifier may have a hydrocarbon chain length of from about 16 to about 20 carbon atoms and from about 20 to about 25 moles of ethoxylate.

In an embodiment, the nonionic emulsifier may have a hydrocarbon chain length of from about 19 to about 11, alternatively from about 9 to about 11 carbon atoms, and from about 2 to about 4 moles of ethoxylate.

In an embodiment, the nonionic emulsifier may comprise a combination of (a) a nonionic emulsifier having a hydrocarbon chain that is branched, has a length of from about 11 to about 15 carbon atoms, and has from about 5 to about 9 moles of ethoxylate; and (b) a nonionic emulsifier having a hydrocarbon chain that has a length of from about 11 to about 13 carbon atoms and has from about 9 to about 12 moles of ethoxylate.

The nanoemulsions used in this invention may be prepared by two different methods: (1) mechanical, and (2) emulsion polymerization.

The first method of preparing the nanoemulsion is the mechanical method in which the nanoemulsion is prepared via the following steps: (1) a primary surfactant is dissolved in water, (2) a silicone is added, and a two-phase mixture is formed, (3) with simple mixing, a co-surfactant is slowly added to the two-phase mixture, until a clear isotropic microemulsion of a siloxane-in-water is formed.

The second method of preparing the nanoemulsion is by emulsion polymerization. Emulsion polymerization methods for making nanoemulsions of polymers involve starting with polymer precursors, i.e., monomers, or reactive oligomers, which are immiscible in water; a surfactant to stabilize polymer precursor droplets in water; and a water soluble polymerization catalyst. Typically, the catalyst is a strong mineral acid such as hydrochloric acid, or a strong alkaline catalyst such as sodium hydroxide. These components are added to water, the mixture is stirred, and polymerization is allowed to advance until the reaction is complete, or the desired degree of polymerization (DP) is reached, and an emulsion of the polymer is formed.

D. Perfume

The concentrated hair care composition may comprise from about 0.5% to about 7%, alternatively from about 1% to about 6%, and alternatively from about 2% to about 5% perfume, by weight of the concentrated hair care composition.

In an embodiment, the concentrated hair care composition may have a silicone to perfume ratio of from about 95:5 to about 50:50, 90:10 to 60:40, 85:15 to 70:30.

Examples of suitable perfumes may be provided in the CTFA (Cosmetic, Toiletry and Fragrance Association) 1992 International Buyers Guide, published by CFTA Publications and OPD 1993 Chemicals Buyers Directory 80th Annual Edition, published by Schnell Publishing Co. A plurality of perfume components may be present in the concentrated hair care composition.

E. High Melting Point Fatty Compounds

The concentrated hair care composition may comprise less than 10% high melting point fatty compounds, alternatively less than 8% high melting point fatty compounds, alternatively less than 6% high melting point fatty compounds, alternatively less than 3% high melting point fatty compound, alternatively may be substantially free of high melting point fatty compounds, and alternatively may comprise 0% high melting point fatty compounds, by weight of the concentrated hair care composition. In an embodiment, the hair care composition may comprise from about 0% to about 8% fatty alcohols, alternatively from about 0.5% to about 6%, alternatively from about 1.0% to about 4%, and alternatively from about 1.5% to about 3.0% fatty alcohols. The concentrated hair care composition may have a silicone to high melting point fatty compounds ratio of from about 100:0 to about 40:60, alternatively from about 100:0 to about 50:50, and alternatively from about 100:0 to about 60:40. In an embodiment the concentrated hair care composition may have a silicone to high melting point fatty compounds ratio of from about 100:0 to about 70:30.

The high melting point fatty compounds have a melting point of about 25° C. or higher, and are selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than about 25° C. Such compounds of low melting point are not intended to be included in this section. Nonlimiting examples of the high melting point compounds are found in *International Cosmetic Ingredient Dictionary*, Fifth Edition, 1993, and *CTFA Cosmetic Ingredient Handbook*, Second Edition, 1992.

The fatty alcohols described herein are those having from about 14 to about 30 carbon atoms, alternatively from about 16 to about 22 carbon atoms. These fatty alcohols are saturated and can be straight or branched chain alcohols. Nonlimiting examples of fatty alcohols include cetyl alcohol, stearyl alcohol, behenyl alcohol, and mixtures thereof.

The fatty acids useful herein are those having from about 10 to about 30 carbon atoms, alternatively from about 12 to about 22 carbon atoms, and alternatively from about 16 to about 22 carbon atoms. These fatty acids are saturated and can be straight or branched chain acids. Also included are diacids, triacids, and other multiple acids. Also included herein are salts of these fatty acids. Nonlimiting examples of fatty acids include lauric acid, palmitic acid, stearic acid, behenic acid, sebacic acid, and mixtures thereof.

The fatty alcohol derivatives and fatty acid derivatives useful herein include alkyl ethers of fatty alcohols, alkoxylated fatty alcohols, alkyl ethers of alkoxylated fatty alcohols, esters of fatty alcohols, fatty acid esters of compounds having esterifiable hydroxy groups, hydroxy-substituted fatty acids, and mixtures thereof. Nonlimiting examples of fatty alcohol derivatives and fatty acid derivatives include materials such as methyl stearyl ether, the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through steareth-10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e., a mixture of fatty alcohols containing predominantly cetyl and stearyl alcohol, wherein the numeric designation indicates the number of ethylene glycol moieties present; C16-C30 alkyl ethers of the ceteth, steareth, and ceteareth compounds just described; polyoxyethylene ethers of behenyl alcohol; ethyl stearate, cetyl stearate, cetyl palmitate, stearyl stearate, myristyl myristate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, glyceryl monostearate, glyceryl distearate, glyceryl tristearate, and mixtures thereof.

In an embodiment, the fatty compound may be a single high melting point compound of high purity. Single compounds of pure fatty alcohols selected may be selected from the group consisting of pure cetyl alcohol, stearyl alcohol, and behenyl alcohol. By "pure" herein, what is meant is that the compound has a purity of at least about 90%, alternatively at least about 95%.

Commercially available high melting point fatty compounds described herein include: cetyl alcohol, stearyl alcohol, and behenyl alcohol having tradenames KONOL series available from Shin Nihon Rika (Osaka, Japan), and NAA series available from NOF (Tokyo, Japan); pure behenyl alcohol having tradename 1-DOCOSANOL available from WAKO (Osaka, Japan), various fatty acids having tradenames NEO-FAT available from Akzo (Chicago, Ill. USA), HYSTRENE available from Witco Corp. (Dublin, Ohio USA), and DERMA available from Vevy (Genova, Italy).

F. Cationic Surfactants

In an embodiment, the concentrated hair care composition may comprise 0%, alternatively from about 0.25% to about 5%, alternatively from about 0.5% to about 4%, and alternatively from about 1% to about 3% cationic surfactants, by weight of the concentrated hair care composition.

The cationic surfactant may be a mono-long alkyl quaternized ammonium salt having the formula (XIII) [from WO2013148778]:

(XIII)

wherein one of $R^{71}$, $R^{72}$ $R^{73}$ a n $R^{74}$ selected from an aliphatic group of from about 14 to about 30 carbon atoms or an aromatic, alkoxy, polyoxyalkylene, alkylamido, hydroxyalkyl, aryl or alkylaryl group having up to about 30 carbon atoms; the remainder of $R^{71}$, $R^{72}$ $R^{73}$ and $R^{74}$ are independently selected from an aliphatic group of from about 1 to about 8 carbon atoms or an aromatic, alkoxy, polyoxyalkylene, alkylamido, hydroxyalkyl, aryl or alkylaryl group having up to about 8 carbon atoms; and X is a salt-forming anion such as those selected from halogen, (e.g., chloride, bromide), acetate, citrate, lactate, glycolate, phosphate, nitrate, sulfonate, sulfate, alkylsulfate, glutamate, and alkyl sulfonate radicals. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. In an embodiment, one of $R^{71}$, $R^{72}$ $R^{73}$ and $R^{74}$ is selected from an alkyl group of from about 14 to about 30 carbon atoms, alternatively from about 16 to about 22 carbon atoms, alternatively from about 16 to about 18 carbon atoms; the remainder of $R^{71}$, $R^{72}$, $R^{73}$, and $R^{74}$ are independently selected from the group consisting of $CH_3$, $C_2H_5$, $C_2H_4OH$, $CH_2C_5H_5$, and mixtures thereof; and (X) is selected from the group consisting of Cl, Br, $CH_3OSO_3$, and mixtures thereof. It is believed that such mono-long alkyl quaternized ammonium salts can provide improved slippery and slick feel on wet hair.

Nonlimiting examples of such mono-long alkyl quaternized ammonium salt cationic surfactants include: behenyl trimethyl ammonium chloride available, for example, with tradename Genamine KDMP from Clariant, with tradename INCROQUAT TMC-80 from Croda and ECONOL TM22 from Sanyo Kasei; stearyl trimethyl ammonium chloride available, for example, with tradename CA-2450 from Nikko Chemicals; cetyl trimethyl ammonium chloride available, for example, with tradename CA-2350 from Nikko Chemicals; behenyltrimethylammonium methyl sulfate, available from FeiXiang; hydrogenated tallow alkyl trimethyl ammonium chloride; stearyl dimethyl benzyl ammonium chloride; and stearoyl amidopropyl dimethyl benzyl ammonium chloride.

Among them, more preferred cationic surfactants are those having a shorter alkyl group, i.e., $C_{16}$ alkyl group. Such cationic surfactant includes, for example, cetyl trimethyl ammonim chloride. It is believed that cationic surfactants having a shorter alkyl group are advantageous for concentrated hair care silicone nanoemulsion compositions of the present invention comprising a cationic surfactant and with improved shelf stability.

G. Water Miscible Solvents

The concentrated hair care compositions described herein may comprise from about 0.1% to about 25%, alternatively from about 0.1% to about 20%, and alternatively from about 0.1% to about 15% of a water miscible solvent, by weight of the concentrated hair care composition. Non-limiting examples of suitable water miscible solvents include polyols, copolyols, polycarboxylic acids, polyesters and alcohols.

Examples of useful polyols include, but are not limited to, glycerin, diglycerin, propylene glycol, ethylene glycol, butylene glycol, pentylene glycol, 1,3-butylene glycol, cyclohexane dimethanol, hexane diol, polyethylene glycol (200-600), sugar alcohols such as sorbitol, manitol, lactitol and other mono- and polyhydric low molecular weight alcohols (e.g., $C_2$-$C_5$ alcohols); mono di- and oligo-saccharides such as fructose, glucose, sucrose, maltose, lactose, and high fructose corn syrup solids and ascorbic acid.

Examples of polycarboxylic acids include, but are not limited to citric acid, maleic acid, succinic acid, polyacrylic acid, and polymaleic acid.

Examples of suitable polyesters include, but are not limited to, glycerol triacetate, acetylated-monoglyceride, diethyl phthalate, triethyl citrate, tributyl citrate, acetyl triethyl citrate, acetyl tributyl citrate.

Examples of suitable dimethicone copolyols include, but are not limited to, PEG-12 dimethicone, PEG/PPG-18/18 dimethicone, and PPG-12 dimethicone.

Examples of suitable alcohols include, but are not limited to ethanol, n-propanol, isopropanol, n-butanol, sec-butanol, tert-butanol, n-hexanol and cyclohexanol.

Other suitable water miscible solvents include, but are not limited to, alkyl and allyl phthalates; napthalates; lactates (e.g., sodium, ammonium and potassium salts); sorbeth-30; urea; lactic acid; sodium pyrrolidone carboxylic acid (PCA); sodium hyraluronate or hyaluronic acid; soluble collagen; modified protein; monosodium L-glutamate; alpha & beta hydroxyl acids such as glycolic acid, lactic acid, citric acid, maleic acid and salicylic acid; glyceryl polymethacrylate; polymeric plasticizers such as polyquaterniums; proteins and amino acids such as glutamic acid, aspartic acid, and lysine; hydrogen starch hydrolysates; other low molecular weight esters (e.g., esters of $C_2$-$C_{10}$ alcohols and acids); and any other water soluble plasticizer known to one skilled in the art of the foods and plastics industries; and mixtures thereof.

In an embodiment, the water miscible solvents may be selected from the group consisting of glycerin, propylene glycol, dipropylene glycol, and mixtures thereof. EP 0283165 B1 discloses other suitable water miscible solvents, including glycerol derivatives such as propoxylated glycerol.

H. Viscosity Modifiers

The concentrated hair care composition described herein may comprise from about 0.1% to about 2%, alternatively from about 0.1% to about 1%, and alternatively from about 0.1% to about 0.5% of a viscosity modifier, by weight of the concentrated hair care composition. Non-limiting examples of suitable viscosity modifiers include water soluble polymers, cationic water soluble polymers, Examples of water soluble polymers include, but are not limited to (1) vegetable based polymers such as gum Arabic, tragacanth gum, galactan, guar gum, carob gum, karaya gum, carrageenan, pectin, agar, quince seed, algal colloid, starch (rice, corn, potato, or wheat), and glycyrrhizinic acid; (2) microorganism-based polymers such as xanthan gum, dextran, succinoglucan, and pullulan; and (3) animal-based polymers such as collagen, casein, albumin, and gelatin. Examples of semi-synthetic water-soluble polymers include (1) starch-based polymers such as carboxymethyl starch and methylhydroxypropyl starch; (2) cellulose-based polymers such as methylcellulose, nitrocellulose, ethylcellulose, methylhydroxypropylcellulose, hydroxyethylcellulose, sodium cellulose sulfate, hydroxypropylcellulose, sodium carboxymethylcellulose (CMC), crystalline cellulose, and cellulose powder; and (3) alginate-based polymers such as sodium alginate and propylene glycol alginate. Examples of synthetic water-soluble polymers include (1) vinyl-based polymers such as polyvinyl alcohol, polyvinyl methyl ether-based polymer, polyvinylpyrrolidone, and carboxyvinyl polymer (CARBOPOL 940, CARBOPOL 941; (2) polyoxyethylene-based polymers such as polyethylene glycol 20,000, polyethylene glycol 6,000, and polyethylene glycol 4,000; (3) copolymer-based polymers such as a copolymer of polyoxyethylene and polyoxypropylene, and PEG/PPG methyl ether; (4) acryl-based polymers such as poly(sodium acrylate), poly(ethyl acrylate), polyacrylamide, polyethylene imines, and cationic polymers. The water-swellable clay minerals are nonionic water-soluble polymers and correspond to one type of colloid-containing aluminum silicate having a triple layer structure. More particular, as examples thereof, mention may be made of bentonite, montmorillonite, beidellite, nontronite, saponite, hectorite, aluminum magnesium silicate, and silicic anhydride.

Examples of cationic water soluble polymers include, but are not limited to (1) quaternary nitrogen-modified polysaccharides such as cation-modified cellulose, cation-modified hydroxyethylcellulose, cation-modified guar gum, cation-modified locust bean gum, and cation-modified starch; (2) dimethyldiallylammonium chloride derivatives such as a copolymer of dimethyldiallylammonium chloride and acrylamide, and poly(dimethylmethylene piperidinium chloride); (3) vinylpyrrolidone derivatives such as a salt of a copolymer of vinylpyrrolidone and dimethylaminoethyl methacrylic acid, a copolymer of vinylpyrrolidone and methacrylamide propyltrimethylammonium chloride, and a copolymer of vinylpyrrolidone and methylvinylimidazolium chloride; and (4) methacrylic acid derivatives such as a copolymer of methacryloylethyldimethylbetaine, methacryloylethyl trimethylammonium chloride and 2-hydroxyethyl methacrylate, a copolymer of methacryloylethyldimethylbetaine, and methacryloylethyl trimethylammonium chloride and methoxy polyethylene glycol methacrylate.

I. Viscosity

The concentrated hair care composition described herein may have a liquid phase viscosity of from about 1 centipoise to about 2,500 centipoise, alternatively from about 5 centipoise to about 2,000 centipoise, alternatively from about 10 centipoise to about 1,500 centipoise, and alternatively from about 15 centipoise to about 1,000 centipoise. In an embodiment, the concentrated hair care composition described herein may have a liquid phase viscosity of from about 1 centipoise to about 15,000 centipoise, alternatively from about 1 centipoise to about 8,000 centipoise, alternatively from about 5 centipoise to about 5,000 centipoise, alternatively from about 10 centipoise to about 2,500 centipoise, alternatively from about 15 centipoise to about 1,500 centipoise, and alternatively from about 20 centipoise to about 1,000 centipoise. In an embodiment, the concentrated hair care composition described herein may have a liquid phase viscosity of from about 200 centipoise to about 15,000 centipoise, alternatively from about 300 centipoise to about 12,000 centipoise, alternatively from about 400 centipoise to about 8,000 centipoise, alternatively from about 500 centipoise to about 5,000 centipoise, and alternatively from about 600 centipoise to about 2,500 centipoise, and alternatively from about 700 centipoise to about 2,000 centipoise.

The viscosity values may be measured employing any suitable rheometer or viscometer at 25.0° C. and at a shear rate of about 2 reciprocal seconds. The viscosities reported herein were measured a Cone/Plate Controlled Stress Brookfield Rheometer R/S Plus, by Brookfield Engineering Laboratories, Stoughton, Mass. The cone used (Spindle C-75-1) has a diameter of 75 mm and 1° angle. The viscosity is determined using a steady state flow experiment at constant shear rate of $2 \, s^{-1}$ and at temperature of 25.0° C. The sample size is 2.5 ml and the total measurement reading time is 3 minutes. The liquid phase viscosity may be measured under ambient conditions and prior to the addition of the propellant.

J. Optional Ingredients

The concentrated hair care composition described herein may optionally comprise one or more additional components known for use in hair care or personal care products, provided that the additional components are physically and chemically compatible with the essential components described herein, or do not otherwise unduly impair product stability, aesthetics or performance. Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1988, 1992. Individual concentrations of such additional components may range from about 0.001 wt % to about 10 wt % by weight of the conditioning composition.

Emulsifiers suitable as an optional ingredient herein include mono- and di-glycerides, fatty alcohols, polyglycerol esters, propylene glycol esters, sorbitan esters and other emulsifiers known or otherwise commonly used to stabilized air interfaces, as for example those used during preparation of aerated foodstuffs such as cakes and other baked goods and confectionary products, or the stabilization of cosmetics such as hair mousses.

Further non-limiting examples of such optional ingredients include preservatives, perfumes or fragrances, cationic polymers, viscosity modifiers, coloring agents or dyes, conditioning agents, hair bleaching agents, thickeners, moisturizers, foam boosters, additional surfactants or nonionic cosurfactants, emollients, pharmaceutical actives, vitamins or nutrients, sunscreens, deodorants, sensates, plant extracts, nutrients, astringents, cosmetic particles, absorbent particles, adhesive particles, hair fixatives, fibers, reactive agents, skin lightening agents, skin tanning agents, antidandruff agents, perfumes, exfoliating agents, acids, bases, humectants, enzymes, suspending agents, pH modifiers, hair colorants, hair perming agents, pigment particles, anti-acne agents, anti-microbial agents, sunscreens, tanning agents, exfoliation particles, hair growth or restorer agents, insect repellents, shaving lotion agents, non-volatile solvents or diluents (water-soluble and water-insoluble), co-solvents or other additional solvents, and similar other materials.

K. Aerosol Foam Dispenser

The aerosol foam dispenser may comprise a reservoir for holding the concentrated hair treatment composition. The reservoir may be made out of any suitable material selected from the group consisting of plastic, metal, alloy, laminate, and combinations thereof. In an embodiment, the reservoir may be for one-time use. In an embodiment, the reservoir may be removable from the aerosol foam dispenser. Alternatively, the reservoir may be integrated with the aerosol foam dispenser. In an embodiment, there may be two or more reservoirs.

In an embodiment, the reservoir may be comprised of a material selected from the group consisting of rigid materials, flexible materials, and combinations thereof. The reservoir may be comprised of a rigid material if it does not collapse under external atmospheric pressure when it is subject to an interior partial vacuum.

In an embodiment, the aerosol foam dispenser may comprise a dip-tube to enable upright dispensing.

In an embodiment, the aerosol foam dispenser may be of the bag on valve type wherein the container comprises an inner bag and an outer container, which encloses the inner bag, while the inner bag has a valve mechanism attached which is movable between an open position and a closed position. The outer container may be formed from metal or plastic or the like, and any of the propellants described herein can be filled in a space between the outer container and the inner bag. The inner bag may be flexible, and can be made from a single material or from a composite material including plastic, which may comprise at least a polymeric layer and a layer which acts as a gas barrier, e.g., made from metal, such as Aluminum. The inner material of the bag may be inert to the contents of the composition, and the inner material may also be impenetrable by the contents of the composition in the bag. The inner bag may comprise a layer of a material which is essentially impermeable to the propellant inside of the bag. The inner bag may comprise a layer of a material which is essentially impermeable to the propellant outside of the bag which generally is not intended to be mixed with the composition in the inner bag during storage.

In an embodiment, the foam has a dosage weight of from about 1 g to about 5 g when dispensed from the aerosol foam dispenser. In another embodiment, the foam has a dosage weight of from about 1 g to about 7 g when dispensed from the aerosol foam dispenser, alternatively from about 2 g to about 6 g, alternatively from about 2.5 g to about 5 g, and alternatively from about 3 g to about 4.5 g. The dosage may be obtained via a single squeeze or actuation of the aerosol foam dispenser, but may be accomplished via two squeezes or actuations of the aerosol foam dispenser.

H. Propellant

The concentrated hair care composition described herein may comprise from about from about 1% to about 6% propellant, alternatively from about 2% to about 5% propellant, and alternatively from about 3% to about 4% propellant, by weight of the concentrated hair care composition. In an embodiment, the concentrated hair care composition described herein may comprise from about from about 1% to about 12% propellant, alternatively from about 2% to about 10% propellant, alternatively from about 3% to about 8% propellant, and alternatively from about 4% to about 6% propellant, by weight of the concentrated hair care composition. The concentrated hair care composition may be dispensed as a foam wherein the foam has a density of from about 0.025 $g/cm^3$ to about 0.30 $g/cm^3$, alternatively from about 0.035 $g/cm^3$ to about 0.20 $g/cm^3$, alternatively from about 0.045 $g/cm^3$ to about 0.15 $g/cm^3$, and alternatively from about 0.055 $g/cm^3$ to about 0.12 $g/cm^3$. In an embodiment, the concentrated hair care composition may be dispensed as a foam wherein the foam as a density of from about 0.025 $g/cm^3$ to about 0.40 $g/cm^3$, alternatively from about 0.035 $g/cm^3$ to about 0.30 $g/cm^3$, alternatively from about 0.045 g/cm³ to about 0.20 g/cm³, and alternatively from about 0.055 g/cm³ to about 0.15 g/cm³.

The propellant may comprise one or more volatile materials, which in a gaseous state, may carry the other components of the concentrated hair care composition in particulate or droplet form. The propellant may have a boiling point within the range of from about −45° C. to about 5° C. The propellant may be liquefied when packaged in convention aerosol containers under pressure. The rapid boiling of the propellant upon leaving the aerosol foam dispenser may aid in the atomization of the other components of the concentrated hair care composition.

Aerosol propellants which may be employed in the aerosol composition may include the chemically-inert hydrocarbons such as propane, n-butane, isobutane, cyclopropane, and mixtures thereof, as well as halogenated hydrocarbons such as dichlorodifluoromethane, 1,1-dichloro-1,1,2,2-tetrafluoroethane, 1-chloro-1,1-difluoro-2,2-trifluoroethane, 1-chloro-1,1-difluoroethylene, 1,1-difluoroethane, dimethyl ether, monochlorodifluoromethane, trans-1,3,3,3-tetrafluoropropene, and mixtures thereof. The propellant may comprise hydrocarbons such as isobutane, propane, and butane—these materials may be used for their low ozone reactivity and may be used as individual components where their vapor pressures at 21.1° C. range from about 1.17 Bar to about 7.45 Bar, alternatively from about 1.17 Bar to about 4.83 Bar, and alternatively from about 2.14 Bar to about 3.79 Bar.

I. Water

The concentrated hair care composition described herein may comprise from about from about 60% to about 90% water, alternatively from about 65% to about 87.5%, alternatively from about 67.5% to about 85%, alternatively from about 70% to about 82.5%, and alternatively from about 72.5% to about 80% water.

Method of Treating Hair

The method of treating the hair described herein comprises (1) providing a concentrated hair care composition, as described herein, in an aerosol foam dispenser, (2) dispensing the concentrated hair care composition from the aerosol foam dispenser as a dosage of foam; (3) applying the foam to the hair; and (4) rinsing the foam from the hair.

Examples & Data

The following examples illustrate the concentrated hair care composition described herein. The exemplified compositions can be prepared by conventional formulation and mixing techniques. It will be appreciated that other modifications of the present invention within the skill of those in the shampoo formulation art can be undertaken without departing from the spirit and scope of this invention. All parts, percentages, and ratios herein are by weight unless otherwise specified. Some components may come from suppliers as dilute solutions. The amount stated reflects the weight percent of the active material, unless otherwise specified.

Three "Clarifying" shampoos are employed in the below examples that were void of high melting point fatty compounds and conditioning agents. One was a Pantene clarifying shampoo and the other two were concentrated foam shampoos. The concentrated foam shampoos may be prepared by mixing together water and surfactants along with any solids that need to be melted at an elevated temperature, e.g. about 75° C. The ingredients are mixed thoroughly at the elevated temperature and then cooled to ambient temperature. Additional ingredients, including electrolytes, polymers, silicone emulsions, preservatives and fragrances may be added to the cooled product.

TABLE 1

Concentrated Aerosol Foam Cleansing Shampoo Composition

| Raw Material | Foam Shampoo 1 | Foam Shampoo 2 |
|---|---|---|
| Sodium Undecyl Sulfate (C11 70% active)[1] | 23.6 | |
| Lauramidopropyl Betaine (LAPB 35% active)[2] | 5.8 | |
| Para Hydroxy Phenyl Butanone[3] | 3.9 | |
| Alkyl polyglucoside[4] | | 25.2 |
| Cocamidopropyl betaine | | 3.9 |
| Polyvinyl alcohol[5] | 1.9 | 1.9 |
| Perfume | 2.3 | 2.3 |
| Citric Acid | 0.3 | 0.3 |
| Preservative (Kathon) | 0.03 | 0.03 |
| Propellant (Aeron-46) | 3.1 | 3.1 |
| Water | q.s. | (q.s.) |
| Weight % of high melting point fatty compounds | 0% | 0% |

[1]Sodium Undecyl Sulfate (C11, Isachem 123S) at 70% active, supplier: P&G
[2]LAPB (Mackam DAB), at 35% active level, supplier: Rhodia
[3]Raspberry Ketone, supplier: Spectrum
[4]EcoSense 919 available from Dow Chemical.
[5]PVA-403 available from Kuraray The following aerosol conditioner compositions may be prepared by weighing distilled water and the aminosilicone emulsions into a stainless steel beaker. The beaker is placed in a water bath on a hot plate while mixing with overhead mixer at 100 to 150 rpm. If fatty alcohols are present in the formula, the cetyl alcohol and stearyl alcohol are added and the mixture is heated to 70-75 C. Cetyltrimethylammonium choloride is then added and mixing speed is increased to 250-350 rpm due to viscosity increase. When the materials are all heated thoroughly and homogenous, the heating is stopped while the mixture is continued to stir. The batch is cooled to 35 C by removing the hot water from the water bath and replacing with cold water. The perfume and Kathon are added and with continued stirring for ~10 minutes. For foaming, propellant Aeron-46 was added to each of the below formulas at a weight ratio of 4 parts Aeron-46 to 96 parts of formula within an aerosol container.

The ability to foam was assessed by shaking the aerosol container for 10 seconds and then seeing if 5 grams could be dispensed into a weigh boat. The foam quality was assessed by spreading the foam and assessing the ability to spread without foam collapse on a qualitative scale (+++ excellent, ++ good, + fair, − poor).

TABLE 2

Concentrated Aerosol Foam Conditioner Composition

| Raw Material | Ex 1 | Ex 2 | Ex 3 | Ex 4 | Ex 5 | Ex 6 | Ex 7 |
|---|---|---|---|---|---|---|---|
| Aminosilicone[1] | 12 | 12 | 12 | 12 | 12 | 12 | 12 |
| Perfume | 2.4 | 2.4 | 3.0 | 3.0 | 3.0 | 3.0 | 3.0 |
| Cetyltrimethylammonium Chloride | | 2.5 | 2.5 | 2.5 | 2.5 | 2.5 | 2.5 |
| Cetyl Alcohol | | | 1.5 | 3.0 | 4.0 | 6.0 | 9 |
| Stearyl Alcohol | | | 1.5 | 3.0 | 4.0 | 6.0 | 9 |
| Preservative (Kathon) | 0.03 | 0.03 | 0.03 | 0.03 | 0.03 | 0.03 | 0.03 |
| Water | (q.s.) | (q.s.) | (q.s.) | (q.s.) | (q.s.) | (q.s.) | (q.s.) |
| Weight ratio of oil to high melting point fatty compounds | 100:0 | 100:0 | 80:20 | 67:33 | 60:40 | 50:50 | 40:60 |
| Viscosity (cp) | <200 | <200 | 810 | 1740 | 5,450 | 12,900 | 33,400 |
| Ability to dispense foam | Yes | Yes | Yes | Yes | Yes | Yes | No |
| Foam Quality | +++ | +++ | +++ | +++ | + | + | None |

[1]Silsoft 253 (20% active) nano-emulsion available from Momentive (10-20 nm)

The foam conditioner compositions of the present invention may be concentrated in silicone (12% by weight) as it has been determined that consumers dose low density foams at approximately ⅓ the dosage of normal conditioners. Accordingly, 12% silicone delivered from the foam delivers about the same dosage of silicone as a normal 4% silicone liquid conditioner. As demonstrated in Table 2, at such a concentrated level of silicone, as the ratio of oil to high melting point fatty compounds decreases, the ability to dispense foam and deliver good foam quality decreases. This is also correlating to viscosity. Importantly, below an oil to high melting point fatty compound ratio of 50:50, the foam was not able to be dispensed (formula was too viscous). Additionally, the ratios of 50:50 and 60:40 had reduced foam quality versus the higher ratios. Accordingly, Examples 1 through 4, with both excellent dispensing and foam quality, were progressed for performance testing as described below.

Concentrated foam conditioners 1-4 in Table 2 were treated onto General Population brown hair switches and dyed hair (dyed with a commercially available level 3 oxidative dye) as part of a regimen with Pantene Pro-V Clarifying Shampoo for up to 6 treatment cycles. Example 2 foam conditioner was also paired with the foam shampoo 1 and foam shampoo 2. As a regimen control, the Pantene Pro-V Clarifying Shampoo was combined with Pantene Anti-Breakage Conditioner. The latter is known to have an aminosilicone content of 2.5% and a total high melting point fatty compounds (cetyl and stearyl alcohols) content of 5.20% for a weight ratio of oil to high melting point fatty compounds of 32.5:67.5. Deposition data, wet and dry combing data, and hair volume data was collected on the hair switches after 6 treatment cycles. Scanning electron microscopy, hair/water contact angles and Atomic Force Microscopy measurements were taken on the hair switches after 6 cycles.

Multiple Cycle Shampoo Plus Conditioner Treatments:
1. Six 4 gram, 8 inch General Population brown hair switches are wet with 100 degrees Fahrenheit water at a sink (bound on root-ends with glue/tape and hanging on metal holder) with a shower head fixture (flow rate is 1.5 gallons per minute) for 15 to 20 seconds.
2. Liquid shampoos are applied at 0.1 grams of product per gram of hair (e.g., Pantene Pro-V Clarifying Shampoo) via a syringe and milked/scrubbed for 30 seconds followed by a 30 seconds shower head rinse (with gentle manipulation at top of switch to ensure uniform rinsing). Concentrated liquid foam shampoos are applied at 0.05 grams of product per gram of hair with a spatula (foam is dispensed in weigh boat and applied weight recorded) and following the same application procedure.
3. Liquid conditioners are applied at a 0.1 grams of product per gram of hair (e.g., Pantene Moisture Renewal Conditioner etc.) via a syringe (weighed on weigh scale) evenly over the hair switch and milked/scrubbed for 30 seconds followed by a 30 seconds shower rinse (with gentle manipulation at top of switch to ensure uniform rinsing). Concentrated liquid foam conditioners are applied at 0.033 grams of product per gram of hair with a spatula (foam is dispensed in weigh boat and applied weight recorded) and following the same application procedure.
4. The hair is then dried in a heat box set at 60 C for ~45 minutes or until mostly dry before starting the next treatment cycle or the completion of the treatment cycles.

For multiple cycle testing, the above procedure is repeated for a set number of times. For instance, for a six cycle test, the above steps 1-4 are repeated six times.

Deposition Data and Deposition Purity (6 Treatment Cycles):

Deposition Purity may be determined by the ratio of silicone deposited per weight of hair to the total deposition of other ingredients per weight of hair. Silicone may be determined by digestion of the hair followed by an analysis with a quantitative elemental technique such as ICP for total silicon and converting to silicone based on the % of silicon in the silicone by weight. The total deposition may be determined by the sum of separate deposition measurements. The separate deposition measurements may include but are not limited to: fatty alcohols, EGDS, quaternized agents and silicone. Typically these measurements involve extracting the hair then separating the ingredients of interest with chromatography and quantifying with an externally calibration based on test solution concentration.

ICP-OES Silicone Hair Digestion Method:

Hair samples treated with different products are submitted as balls of hair with an average sample size of 0.1 g. These hair samples are then digested using a single reaction chamber microwave digestion system (Milestone Inc., Shelton, Conn.) using a 6:1 $HNO_3:H_2O_2$ mixture and an aliquot of methyl isobutyl ketone (MIBK) in Teflon digestion vessels. A gentle digestion program with a ramp to 95° C. and a manual vent after cooling below 30° C. is used to facilitate retention of silicon. After dilution to volume, the samples are run against an inorganic silicon calibration curve produced on an Optima 8300 ICP-OES system (Perkin Elmer, Waltham, Mass.) run in the axial mode. The silicon values determined are converted to a concentration of silicone polymer-equivalents deposited on the hair sample using the theoretical silicon concentration of the polymer provided by the manufacturer. An untreated hair sample is analyzed to determine the background concentration of silicon to allow correction if needed. Another untreated hair sample is spiked with a known amount of polymer and analyzed to ensure recovery of the polymer and verify the analysis.

TABLE 3

Results of Deposition and Deposition Purity on General Population Hair after 6 treatment cycles

| Regimen | Fatty Alcohol Deposition (ppm) | Amino-silicone Deposition (ppm) [% RSD] | Alkyl Quat Deposition (ppm) | Amino-silicone-to-fatty alcohol ratio | Oil Deposition Purity | Total Deposition (ppm) |
|---|---|---|---|---|---|---|
| Clarifying Shampoo plus Pantene Anti-breakage Conditioner | 1749 +/− 81 | 1557 +/− 844 [54%] | 26 +/− 2 | 0.9 | 47% | 3332 |
| Clarifying Shampoo plus Ex 1 Conditioner | 3.0 +/− 8 | 1341 +/− 449 [33%] | 6 +/− 0.4 | 447 | 99% | 1350 |
| Clarifying Shampoo plus Ex 2 Conditioner | 14 +/− 4 | 1040 +/− 105 [10%] | 140 +/− 13 | 74 | 87% | 1194 |
| Clarifying Shampoo plus Ex 3 Conditioner | 488 +/− 23 | 1334 +/− 82 [6%] | 94 +/− 13 | 2.7 | 70% | 1916 |
| Clarifying Shampoo plus Ex 4 Conditioner | 668 +/− 36 | 1546 +/− 67 [4%] | 67 +/− 10 | 2.3 | 68% | 2281 |
| Foam Shampoo 1 plus Ex 2 Conditioner | 8 +/− 3 | 934 +/− 60 [6%] | 126 +/− 9 | 117 | 87% | 1068 |
| Foam Shampoo 2 plus Ex 2 Conditioner | 1 +/− 5 | 996 +/− 58 [4%] | 158 +/− 12 | 996 | 86% | 1155 |

General Population Hair

The Table 3 deposition data on general population hair after 6 treatment cycles demonstrates the regimens involving a foam conditioner of the present invention deposit high levels of aminosilicone onto hair (900 to 1,600 ppm versus 1,600 ppm for the liquids control regimen), but importantly with significantly less fatty alcohol co-deposits (1 to 700 ppm fatty alcohols versus 1,557 ppm for the liquid control regimen). Correspondingly, the measured oil deposition purity was much higher for the regimens of the present invention (68% to 99% purity) versus the liquid regimen control (47% purity).

Dyed Hair

TABLE 4

Results of Deposition and Deposition Purity on Dyed Hair after 6 treatment cycles

| Regimen | Fatty Alcohol Deposition (ppm) | Amino-silicone Deposition (ppm) | Alkyl Quat Deposition (ppm) | Amino-silicone-to-fatty alcohol ratio | Oil Deposition Purity | Total Deposition (ppm) | Dyed-to-General Population Hair Deposition Ratio (×100%) |
|---|---|---|---|---|---|---|---|
| Clarifying Shampoo plus Pantene Anti-breakage Conditioner | 1532 +/− 84 | 1057 +/− 260 [25%] | 32 +/− 3 | 0.7 | 40% | 2621 | 68% |
| Clarifying Shampoo plus Ex 1 Conditioner | 31 +/− 16 | 1464 +/− 78 [5%] | 11 +/− 0 | 47 | 97% | 1506 | 109% |
| Clarifying Shampoo plus Ex 2 Conditioner | 31 +/− 16 | 1385 +/− 149 [11%] | 149 +/− 26 | 45 | 88% | 1565 | 133% |
| Clarifying Shampoo plus Ex 3 Conditioner | 444 +/− 12 | 2040 +/− 147 [7%] | 115 +/− 25 | 4.6 | 78% | 2599 | 153% |
| Clarifying Shampoo plus Ex 4 Conditioner | 636 +/− 41 | 2225 +/− 108 [5%] | 84 +/− 13 | 3.5 | 76% | 2945 | 144% |
| Foam Shampoo 1 plus Ex 2 Conditioner | 7 +/− 17 | 1484 +/− 47 [3%] | 133 +/− 15 | 212 | 91% | 1624 | 159% |
| Foam Shampoo 2 plus Ex 2 Conditioner | 9 +/− 10 | 1479 +/− 103 [7%] | 195 +/− 16 | 164 | 88% | 1683 | 148% |

The Table 4 deposition data on dyed hair after 6 treatment cycles demonstrates the regimens involving a foam conditioner of the present invention to deposit high levels of aminosilicone onto hair (1,385 to 2,225 ppm versus 1,057 ppm for the liquids control regimen), but importantly with significantly less fatty alcohol co-deposits (7 to 636 ppm fatty alcohols versus 1,557 ppm for the liquid control regimen). Correspondingly, the measured oil deposition purity was much higher for the regimens of the present invention (76% to 97% purity) versus the liquid regimen control (40% purity). Moreover, the regimens involving a foam conditioner of the present invention also deposit significantly greater amount of silicone onto the more polar dyed hair than on general population hair (dyed to general population hair deposition ratios of 109% to 159%) versus the liquid regimen control which deposited less silicone on the more polar dyed hair (dyed to general population hair deposition ratios of 68%).

General Population Hair Wet Combing, Dry Combing and Hair Volume Data (6 Treatment Cycles):

Wet combing, dry combing and hair volume was assessed of the hair tresses after the 6 treatment cycles via a sensory panel encompassing 12 individuals.

Wet Combing Test (on the Day of the Final Treatment Cycle):

After the last treatment cycle, the treated hair tresses were wrapped in aluminum foil and labeled in groups. During the panel, a hair tress from each leg grouping was hung on a metal bar and with each switch being detangled with the wider spacing teeth on a professional comb. The panelists then evaluated the ease of wet combing of the switches using the 'small end' of a professional comb (using gloved hand to stabilize switch while combing if needed) and record scores on the provided evaluation form (0-10 scale). After all 5 sets of hair have been combed (2 panelists per hair set), hang carts with hair in CT room (50% RH, 70 F).

Dry Combing Test (at Least One Day after the Wet Combing Test):

The dried hair switches from each treatment group were placed in separate metal holders hanging side by side on a metal bar. The panelists evaluated the ease of dry combing of the switches using the 'small end' of a professional comb and record scores on the provided evaluation form (0-10 scale; 2 panelists per hair set).

General Population Hair

TABLE 5

Wet/Dry Combing and Hair Volume on General Population Hair after 6 treatment cycles

| Regimen | Regimen weight ratio of oil to high melting point fatty compounds | Wet Combing | Dry Combing | Hair Volume |
| --- | --- | --- | --- | --- |
| Clarifying Shampoo Control | — | 2.0 | 2.6 | 8.5 |
| Clarifying Shampoo plus Pantene Anti-breakage Conditioner | 32.5:67.5 | 8.2 | 9.8 | 4.3 |
| Clarifying Shampoo plus Ex 1 Conditioner | 100:0 | 9.0 | 8.0 | 7.6 |
| Clarifying Shampoo plus Ex 2 Conditioner | 100:0 | 9.4 | 8.2 | 5.6 |
| Clarifying Shampoo plus Ex 3 Conditioner | 80:20 | 9.3 | 8.6 | 4.6 |
| Clarifying Shampoo plus Ex 4 Conditioner | 67:33 | 9.2 | 8.3 | 3.6 |
| Foam Shampoo 1 plus Ex 2 Conditioner | 100:0 | 8.6 | 7.1 | 6.0 |
| Foam Shampoo 2 plus Ex 2 Conditioner | 100:0 | 8.9 | 7.5 | 7.5 |

The above data on general population hair after 6 treatment cycles demonstrates the regimens involving a foam conditioner of the present invention provide acceptable wet combing performance (from 8.2 to 9.4 average scores) and dry combing performance (from 7.1 to 8.6 average scores) versus the liquid control regimen (wet combing of 8.2 and dry combing of 9.8). But, importantly the regimens involving a foam conditioner of the present invention were able to do this with very good hair volume performance after the end of the treatment cycles (hair volume average scores of 3.6 to 7.6) relative to the liquid regimen control (hair volume of 4.3). Also, the hair volume trends with the weight ratio of oil to high melting point fatty compounds within the regimen compositions (with 100:0 ratios providing the best hair volume performance). This is hypothesized to be due to significantly less co-deposits of high melting point fatty compounds.

Dyed Hair

TABLE 6

Wet/Dry Combing and Hair Volume on Dyed Hair after 6 treatment cycles

| Regimen | Regimen weight ratio of oil to high melting point fatty compounds | Wet Combing | Dry Combing | Hair Volume |
| --- | --- | --- | --- | --- |
| Clarifying Shampoo Control | — | 1.6 | 1.5 | 5.5 |
| Clarifying Shampoo plus Pantene Anti-breakage Conditioner | 32.5:67.5 | 8.0 | 9.6 | 4.1 |
| Clarifying Shampoo plus Ex 1 Conditioner | 100:0 | 9.3 | 7.6 | 8.1 |
| Clarifying Shampoo plus Ex 2 Conditioner | 100:0 | 9.8 | 8.5 | 4.3 |
| Clarifying Shampoo plus Ex 3 Conditioner | 80:20 | 9.4 | 8.5 | 5.9 |
| Clarifying Shampoo plus Ex 4 Conditioner | 67:33 | 9.3 | 8.7 | 3.9 |
| Foam Shampoo 1 plus Ex 2 Conditioner | 100:0 | 8.7 | 7.7 | 6.2 |
| Foam Shampoo 2 plus Ex 2 Conditioner | 100:0 | 8.6 | 7.5 | 7.1 |

*representative of oxidatively damaged hair

The Table 6 data on dyed hair after 6 treatment cycles demonstrates the regimens involving a foam conditioner of the present invention to provide very good wet combing performance (from 8.6 to 9.3 average scores) and dry combing performance (from 7.5 to 8.5 average scores) comparable to the liquid control regimen (wet combing of 8.0 and dry combing of 9.6). But, importantly the regimens involving a foam conditioner of the present invention were able to do this with good hair volume performance after the end of the treatment cycles (hair volume average scores of 3.9 to 8.1) relative to the liquid regimen control (hair volume of 4.1). Also, the hair volume trends with the weight ratio of oil to high melting point fatty compounds within the regimen compositions (with 100:0 ratios providing the best hair volume performance). This is hypothesized to be due to significantly less co-deposits of high melting point fatty compounds.

Scanning Electron Microscopy (6 treatment cycles)

Ten to twelve general population hair strands with 1 cm length hair from each treatment were mounted on SEM sample holder, coated with Au/Pd for 45 seconds for conductivity, transferred sample holder into SEM chamber, and used Hitachi S4700 Field Emission High Resolution SEM for imaging analysis at 3 kv with built-in Bruker Quantax Esprit SDD for EDS (Energy Dispersive X-ray Spectrometry) analysis for elemental information at 5 kv. The high-resolution image visualized the details of topography, hair structure and the deposition on its surface. EDS revealed the existence of elements of and correlated to the image topography.

Figure 2:
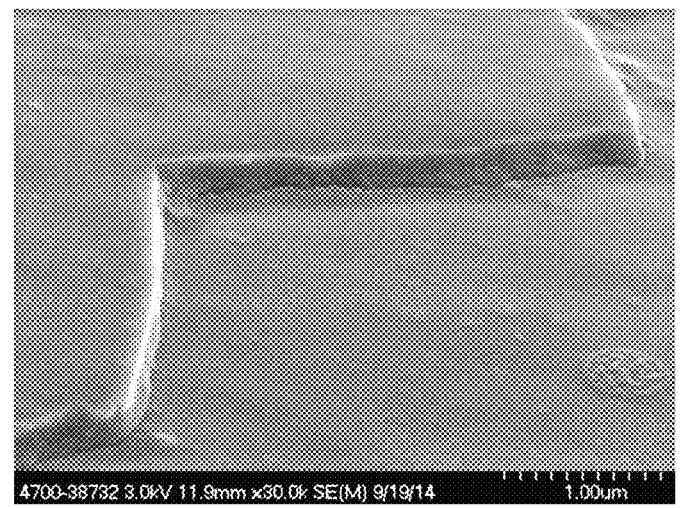
FIG. 2 is an SEM image of hair treated with a Pantene Clarifying Shampoo plus the aerosol foam conditioner of Example 1 from Table 2.
Figure 3:
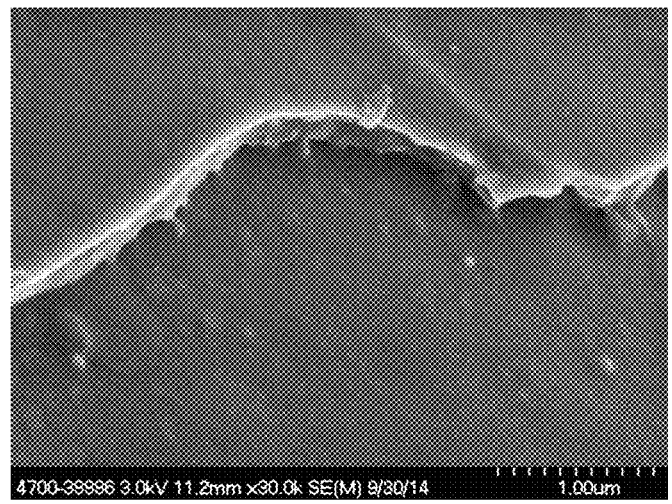
FIG. 3 is an SEM image of hair treated with a Pantene Clarifying Shampoo plus the aerosol foam conditioner of Example 2 from Table 2.
Figure 4:
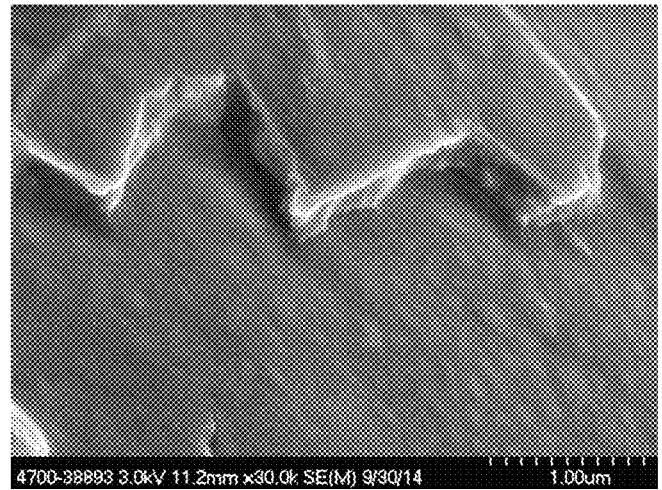
FIG. 4 is an SEM image of hair treated with a Pantene Clarifying Shampoo plus the aerosol foam conditioner of Example 3 from Table 2.
Figure 5:
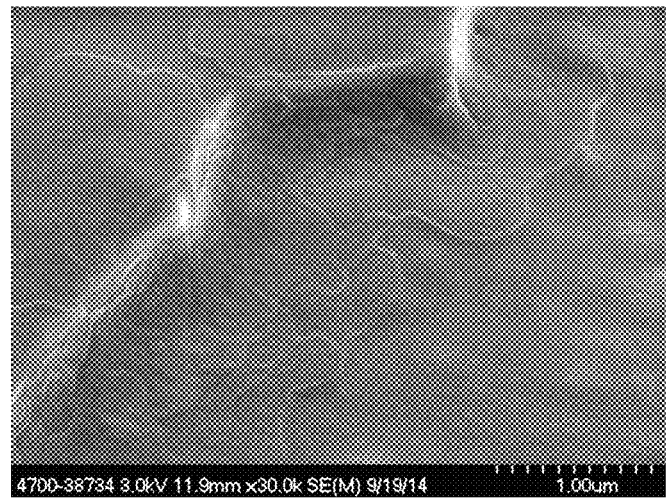
FIG. 5 is an SEM image of hair treated with a Pantene Clarifying Shampoo plus the aerosol foam conditioner of Example 4 from Table 2.
Figure 6:
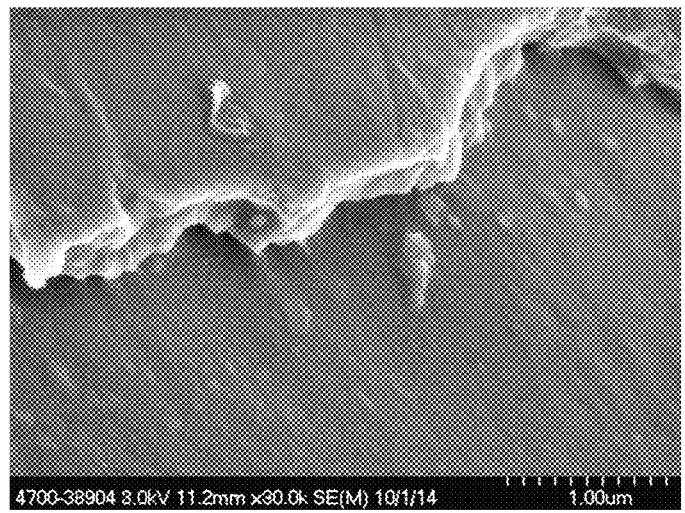
FIG. 6 is an SEM image of hair treated with Foam Shampoo 1 from Table 1 plus the aerosol foam conditioner of Example 2 from Table 2.
Figure 7:
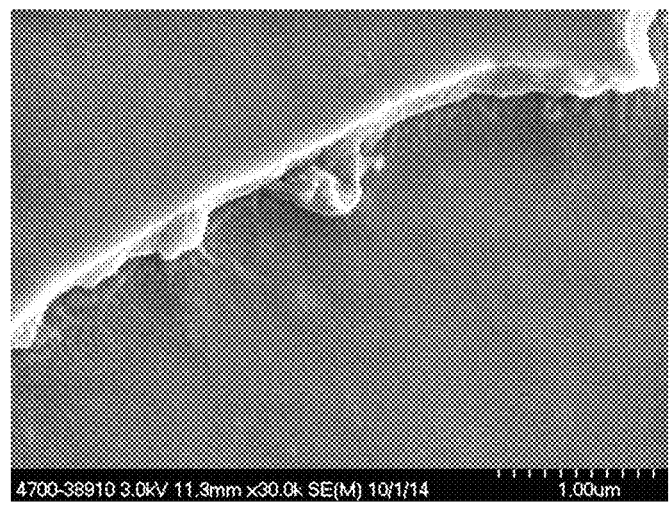
FIG. 7 is an SEM image of hair treated with Foam Shampoo 2 from Table 1 plus the aerosol foam conditioner of Example 2 from Table 2.

The SEM images after 6 treatment cycles on general population hair in FIGS. 1-7 demonstrate the regimens involving a foam conditioner of the present invention to provide surface deposits with improved morphology (thinner, smoother and more even deposition) versus the liquid control regimen (irregular deposits that are thicker, not smooth and lacking even deposition). This is hypothesized to be due to significantly less co-deposits of high melting point fatty compounds (from 68% to 99% oil deposition purity) versus the liquid regimen control (from 40% to 47% oil deposition purity).

Hair/Water Contact Angle and Time of Flight SIMS (6 Treatment Cycles)

Hair/Water Contact Angle (General population hair): Approximately 2 cm segments from root, middle and tip were immersed in hexadecane and water root end first. The first 200 μm of the segment was ignored. Every 100 μm longitudinally up the length of the hair segment was analyzed for wetting force. Wilhelmy equation of state for rods was used to convert wetting force into contact angle. Hair diameters were measured optically.

Time-of-Flight Secondary Ion Mass Spectrometry (General Population Hair):

ToF-SIMS provides mass spectrum and imaging analysis on the hair surfaces and the information collected represents the chemical structure and distribution information from the outmost 3 nm of the sample's surface. In detail, single hair fibers were mounted on a stainless steel sample holder and transferred to an ultra high vacuum system (10^-8-10^-9 torr) of the ToF-SIMS instrument (ION-TOF 4, ION TOF, Germany). In spectrum mode, characteristic signals were selected for each silicone containing species present on the hair surface and semi-quantitative comparison from sample to sample was done by normalizing the characteristic signals to total ion intensity from the same spectrum. Selected characteristic signals were further used to image the distribution of chemicals on hair surfaces using high resolution imaging mode of the instrument.

TABLE 7

Advancing and Receding Contact Angles

| Regimen | Advancing Contact Angle | Receding Contact Angle |
|---|---|---|
| Clarifying Shampoo Control | 91.1 +/− 4.9 | 38.3 +/− 12.1 |
| Clarifying Shampoo plus Pantene Antibreakage Conditioner | 99.2 +/− 0.4 | 58.4 +/− 1.7 |
| Clarifying Shampoo plus Ex 1 Conditioner | 116.6 +/− 0.5 | 69.0 +/− 1.1 |
| Clarifying Shampoo plus Ex 2 Conditioner | 108.9 +/− 3.2 | 70.8 +/− 0.9 |
| Clarifying Shampoo plus Ex 3 Conditioner | 110.6 +/− 0.1 | 69.5 +/− 0.1 |
| Clarifying Shampoo plus Ex 4 Conditioner | 108.5 +/− 0.7 | 66.8 +/− 1.9 |
| Foam Shampoo 1 plus Ex 2 Conditioner | 110.5 +/− 0.9 | 68.1 +/− 1.1 |
| Foam Shampoo 2 plus Ex 2 Conditioner | 115.5 +/− 0.2 | 69.5 +/− 1.9 |

The Table 7 advancing and receding contact angles after 6 treatment cycles on general population hair demonstrates the regimens involving a foam conditioner of the present invention to provide significantly greater hair surface hydrophobicity (advancing contact angles from 108.5 degrees to 116.6 degrees and receding contact angles from 66.8 degrees to 70/8 degrees) versus the liquid control regimen (advancing contact angle of 99.2 degrees and a receding contact angle of 58.4 degrees). Without being bound to theory, this is hypothesized to be due to significantly less co-deposits of high melting point fatty compounds (from 68% to 99% oil deposition purity) versus the liquid regimen control (from 40% to 47% oil deposition purity). Importantly, the contact angle data also correlates with the TOF-SIMS silicone mapping as can be seen in the above image wherein the regimens involving a foam conditioner of the present invention can be seen to have greater TOF-SIMS silicone intensity (seen as increased brightness over the black background) relative to the liquid regimen control.

Atomic Force Microscopy (6 Treatment Cycles)

Samples were prepared for AFM analysis by selecting three hairs (from treated general population hair) and adhering them to a glass microscope slide with quick curing epoxy; the analysis region was approximately the middle of the hair. AFM images were collected from one location on two fibers for each sample. Images were collected in tapping (intermittent contact) mode with a Field of View (FOV) of 40×20 mm and 512×256 pixels, yielding a spatial resolution of 78 nm. Image tilt was corrected with a first order plane fit. Force Curves were collected over the same areas imaged by AFM. Maps consisted of an array of 10 by 10 individual force curves uniformly distributed over the FOV. Adhesion values were extracted from force curves using instrument manufacturer's software. Higher magnification images were collected for a field of view of, approximately, 5×2.5 mm, yielding a resolution of 10 nm. Image tilt was corrected by a first order plain fit. Force maps were collected for several of these regions. Roughness values were obtained from height images that had been corrected for tilt (using a first order plane fit), followed by a second order plane fit to remove the hair curvature from the data. Finally another first order plane was fit to a single cuticle surface in order to remove cuticle slope from the data. (On Modify Panel, Planefit Tab, select Include Points, then draw freehand ROI on cuticle. Only the drawn ROI will be included in the mask.) Roughness was calculated over a 2.5 mm square area from six regions in each image. Step from one cuticle to next was excluded from roughness calculation; generally, it was attempted to include areas with deposition in the calculation. The AFM probe type was Olympus AC 160 (lot 9C3002) silicon diving board. Cantilever length is 160 nm; nominal radius for a new tip is less than 15 nm. Probes were calibrated for force measurements. One probe was used for all measurements.

TABLE 8

AFM Deposit Thickness

|  | Clarifying Shampoo plus Pantene Antibreakage Conditioner | Clarifying Shampoo plus Ex 1 Conditioner | Clarifying Shampoo plus Ex 4 Conditioner |
| --- | --- | --- | --- |
| Num Images | 3 | 3 | 4 |
| Num Points | 710 | 544 | 611 |
| Avg (nm) | 32.8 | 15.4 | 15.1 |
| Std Dev (nm) | 55.0 | 9.5 | 9.8 |
| Min (nm) | 3.6 | 5.5 | 3.8 |
| Max (nm) | 439.4 | 80.2 | 100.1 |

The AFM images after 6 treatment cycles on general population hair demonstrates the regimens involving a foam conditioner of the present invention to provide surface deposits with improved morphology (thinner, smoother and more even deposition) versus the liquid control regimen (irregular deposits that are thicker, not smooth and lacking even deposition). Additionally, the AFM was able to quantify the thickness of the deposits and demonstrating the regimens involving a foam conditioner of the present invention to provide significantly thinner deposits (averages of 15.1+/−9.8 nanometers and 15.4+/−9.5 nanometers) versus the liquid control regimen (32.8+/−55 nanometers). Without being bound to theory, this is hypothesized to be due to significantly greater purity of deposition (from 68% to 99% oil deposition purity) versus the liquid regimen control (from 40% to 47% oil deposition purity) and enabling the silicone to spread better as the continuous phase of the deposit versus as the dispersed phase within a continuous phase of high melting point fatty compounds which do not spread nearly as well due to their high melting point (wax-like consistency).

Additional Examples

The following aerosol conditioner compositions in Tables 9 and 10 may be prepared by weighing distilled water and the aminosilicone emulsions into a stainless steel beaker. The beaker is placed in a water bath on a hot plate while mixing with overhead mixer at 100 to 150 rpm. If fatty alcohols are present in the formula, the cetyl alcohol and stearyl alcohol are added and the mixture is heated to 70-75 C. The behentrimonium methosulfate is then added and mixing speed is increased to 250-350 rpm due to viscosity increase. When the materials are all heated thoroughly and homogenous, the heating is stopped while the mixture is continued to stir. The batch is cooled to 35 C by removing the hot water from the water bath and replacing with cold water. The perfume and Kathon are added and with continued stirring for ~10 minutes. For foaming, propellant Aeron-46 is added to each of the below formulas at a weight ratio of 4 parts Aeron-46 to 96 parts of formula within an aerosol container.

TABLE 9

| Raw Material | Ex 8 | Ex 9 | Ex 10 | Ex 11 | Ex 12 | Ex 13 |
| --- | --- | --- | --- | --- | --- | --- |
| Aminosilicone[1] | 8 | 4 | 2 | 0 | 8 | 4 |
| Aminosilicone[2] |  | 4 | 2 | 4 |  | 4 |
| Perfume | 2.0 | 2.0 | 2.0 | 2.0 | 2.0 | 2.0 |
| Behentrimonium methosulfate | 4.3 | 4.3 | 4.3 | 4.3 | 4.3 | 4.3 |
| Cetyl Alcohol | 0.86 | 0.86 | 0.86 | 0.86 | 0.86 | 0.86 |
| Stearyl Alcohol | 2.15 | 2.15 | 2.15 | 2.15 | 2.15 | 2.15 |
| Hydroxyethyl cellulose[3] | 0.00 | 0.00 | 0.00 | 0.00 | 1.00 | 0.5 |
| Citric Acid | 0.02 | 0.02 | 0.02 | 0.02 | 0.02 | 0.02 |
| Benzyl Alcohol | 0.4 | 0.4 | 0.4 | 0.4 | 0.4 | 0.4 |
| Disodium EDTA | 0.13 | 0.13 | 0.13 | 0.13 | 0.13 | 0.13 |
| Preservative (Kathon) | 0.03 | 0.03 | 0.03 | 0.03 | 0.03 | 0.03 |
| Water | (q.s.) | (q.s.) | (q.s.) | (q.s.) | (q.s.) | (q.s.) |
| Weight ratio of oil to high melting point fatty compounds | 73:27 | 73:27 | 57:43 | 57:43 | 73:27 | 73:27 |
| Viscosity (cp) | 591 | 756 | 1461 | 9505 | 6830 | 3202 |

[1]Silsoft 253 (20% active) nano-emulsion available from Momentive (10-20 nm)
[2]Y17045 (100% active) available experimentally from Momentive
[3]Natrosol 250 HHR available from Ashland Chemicals.

TABLE 10

| Raw Material | Ex 14 | Ex 15 | Ex 16 | Ex 17 | Ex 18 | Ex 19 |
| --- | --- | --- | --- | --- | --- | --- |
| Amino morpholino silicone[4] | 8 | 12 | 16 |  |  |  |
| Aminosilicone[5] |  |  |  | 8 | 12 | 16 |
| Perfume | 2.0 | 2.0 | 2.0 | 2.0 | 2.0 | 2.0 |
| Behentrimonium methosulfate | 4.3 | 4.3 | 4.3 | 4.3 | 4.3 | 4.3 |
| Cetyl Alcohol | 0.86 | 0.86 | 0.86 | 0.86 | 0.86 | 0.86 |
| Stearyl Alcohol | 2.15 | 2.15 | 2.15 | 2.15 | 2.15 | 2.15 |
| Citric Acid | 0.02 | 0.02 | 0.02 | 0.02 | 0.02 | 0.02 |
| Benzyl Alcohol | 0.4 | 0.4 | 0.4 | 0.4 | 0.4 | 0.4 |
| Disodium EDTA | 0.13 | 0.13 | 0.13 | 0.13 | 0.13 | 0.13 |
| Preservative (Kathon) | 0.03 | 0.03 | 0.03 | 0.03 | 0.03 | 0.03 |
| Water | (q.s.) | (q.s.) | (q.s.) | (q.s.) | (q.s.) | (q.s.) |
| Weight ratio of oil to high melting point fatty compounds | 73:27 | 80:20 | 84:16 | 73:27 | 80:20 | 84:16 |

[4]BELSIL® ADM 8301 E (20% active) nano-emulsion available from Wacker (<50 nm)
[5]CE-8170 Microemulsion (20% active) available from Dow Corning (<50 nm)

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of treating the hair, the method comprising:
    a. providing a concentrated hair care composition in an aerosol foam dispenser, wherein the concentrated hair care composition comprises:
        i. from about 10% to about 14%, by weight of the concentrated hair care composition, of an aminopropylaminoethylpolysiloxane; wherein the particle size of the aminopropylaminoethylpolysiloxane is from about 10 nm to about 60 nm;
        ii. less than 8%, by weight of the concentrated hair care composition, of a mixture of cetyl alcohol and stearyl alcohol;
        iii. from about 0.5% to about 4%, by weight of the concentrated conditioner composition, of a cetyl trimethyl ammonium chloride;
        iv. from about 1% to about 12% propellant, by weight of the concentrated hair care composition;
        v. from about 0.5% to about 7%, by weight of the concentrated hair care composition, of a perfume;
        vii. from about 60% to about 90% water, by weight of the concentrated hair care composition;
    b. dispensing the concentrated hair care composition from the aerosol foam dispenser as a foam;
    c. applying the foam to the hair; and
    d. rinsing the foam from the hair.

2. The method of claim 1, wherein the concentrated hair care composition has a liquid phase viscosity of from about 200 centipoise to about 2000 centipoise.

3. The method of claim 1, wherein the concentrated hair care composition comprises from about 2% to about 12%, by weight of the concentrated hair care composition, of a nonionic emulsifier.

4. The method of claim 1, wherein the concentrated hair care composition comprises less than 6%, by weight of the concentrated hair care composition, of the mixture of cetyl alcohol and stearyl alcohol.

5. The method of claim 1, wherein the concentrated hair care composition comprises from about 1% to about 6%, by weight of the concentrated hair care composition, of the perfume.

6. The method of claim 1, wherein the foam has a dosage weight of from about 1 g to about 5 g when dispensed from the aerosol foam dispenser.

7. The method of claim 1, wherein the density of the foam is from about 0.035 g/cm$^3$ to about 0.20 g/cm$^3$.

8. The method of claim 1, further comprising the step of washing the hair with a shampoo before providing the concentrated conditioner.

* * * * *